United States Patent
McGlone

(10) Patent No.: US 12,097,181 B2
(45) Date of Patent: Sep. 24, 2024

(54) SWINE MATERNAL NEONATAL PHEROMONE

(71) Applicant: Texas Tech University System, Lubbock, TX (US)

(72) Inventor: John J. McGlone, Slaton, TX (US)

(73) Assignee: Texas Tech University System, Lubbock, TX (US)

( * ) Notice: Subject to any disclaimer, the term of this patent is extended or adjusted under 35 U.S.C. 154(b) by 0 days.

(21) Appl. No.: 17/859,864

(22) Filed: Jul. 7, 2022

(65) Prior Publication Data

US 2022/0354823 A1    Nov. 10, 2022

Related U.S. Application Data

(62) Division of application No. 17/027,057, filed on Sep. 21, 2020.

(60) Provisional application No. 62/902,643, filed on Sep. 19, 2019.

(51) Int. Cl.
*A61K 31/404* (2006.01)
*A61K 9/00* (2006.01)
*A61K 31/20* (2006.01)
*A61P 25/00* (2006.01)
*A61P 43/00* (2006.01)

(52) U.S. Cl.
CPC .......... *A61K 31/404* (2013.01); *A61K 9/0056* (2013.01); *A61K 31/20* (2013.01); *A61P 25/00* (2018.01); *A61P 43/00* (2018.01)

(58) Field of Classification Search
CPC .... A61K 31/404; A61K 9/0056; A61K 31/20; A61P 25/00; A61P 43/00
See application file for complete search history.

(56) References Cited

U.S. PATENT DOCUMENTS

| | | |
|---|---|---|
| 6,169,113 B1 | 1/2001 | Pageat |
| 6,384,252 B1 | 5/2002 | Paget |
| 8,802,209 B2 | 8/2014 | Lacoste et al. |
| 8,808,721 B2 | 8/2014 | Banfield et al. |
| 8,933,126 B2 | 1/2015 | Deminiere et al. |
| 8,999,395 B2 | 4/2015 | Zanichelli et al. |
| 10,058,526 B2 | 8/2018 | Lacoste |
| 11,331,296 B2 | 5/2022 | Lacoste et al. |
| 2010/0176136 A1 | 7/2010 | Lacoste et al. |
| 2011/0077301 A1 | 3/2011 | Deminiere et al. |

(Continued)

FOREIGN PATENT DOCUMENTS

| | | |
|---|---|---|
| CN | 112370528 A | 2/2021 |
| EP | 3124020 A1 | 2/2017 |

OTHER PUBLICATIONS

Liliana Salvatore "Instrumental and Sensory Analysis of Volatile Organic Compounds in Porcine Adipose Tissue," (2003), and Gries et al. (US 2016/0316750 A1, Nov. 3, 2016). (Year: 2003).*

(Continued)

*Primary Examiner* — Bethany P Barham
*Assistant Examiner* — K. A. Ketcham
(74) *Attorney, Agent, or Firm* — POLSINELLI PC

(57) ABSTRACT

Provided herein are maternal neonatal pheromonal agents capable of reducing aggression and improving feeding behavior in a pig. Compositions comprising the pheromonal agents and methods of using the agents to reduce aggression and improve feeding behavior and weight gain in the pig are also provided.

10 Claims, 7 Drawing Sheets

(56) References Cited

U.S. PATENT DOCUMENTS

2015/0038544 A1     2/2015  Gillessen et al.
2016/0316750 A1*   11/2016  Gries et al. ............ A01N 43/50
2017/0135976 A1*    5/2017  Lacoste .................. A61P 43/00

OTHER PUBLICATIONS

Archer et al. (2022) Olfactory enrichment using a maternal pheromone improved post-weaning pig performance and behavior. Front. Vet. Sci. 9:965370.doi: 10.3389/fvets.2022.965370 pp. 1-13 (Year: 2022).*
Marshall (Sci Nat 103, 59, 2016) (Year: 2016).*
Keeling Proc Natl Acad Sci U S A. Apr. 15, 2003; 100(8): 4486-4491) (Year: 2003).*
American Chemical Society (Skatole, Mar. 5, 2012. abstract).
Pauly, C., Spring, P., O'Doherty, J., Ampuero Krageten, S., & Bee, G. (2009). Growth performance, carcass characteristics and meat quality of group-penned surgically castrated, immunocastrated (Improvac) and entire male bigs and individually penned entire male pigs. Animal, 3(7), 1057-1066. doi: 10.1017/S1751731109.
Edgar O. Aviles Rosa, B.S., M.S.; The effect of Swine's semiochemicals on pigs' behavior, physiology and production, dissertation May 2019 (Year: 2019).

* cited by examiner

SWINE MATERNAL NEONATAL PHEROMONE

CROSS-REFERENCE TO RELATED APPLICATIONS

This application claims priority from Provisional Application Ser. No. 62/902,643, filed Sep. 19, 2019 and Nonprovisional application Ser. No. 17/027,057 filed Sep. 21, 2020, the contents of which are hereby incorporated by reference in their entirety.

FIELD OF THE INVENTION

The present invention relates generally to maternal pheromonal agents for reducing aggression and improving feeding behavior and weight gain and overall health and performance in a pig.

BACKGROUND OF THE INVENTION

Sows produce maternal odors and compounds that the piglets learn shortly after birth. These maternal-neonatal pheromones can improve piglet milk consumption, feeding and social behavior, and general health. For instance, maternal-neonatal pheromones can reduce fighting and increase feeding behavior of the piglets. Extreme aggression in lactating piglets can result in substantial losses due to lameness, infections, and death, thereby decreasing efficiency of production, increasing labor and space requirements, and reducing profits. The time spent on fighting comes directly at the cost of the time spent on feeding. Solutions other than building housing modification are costly and only partially effective. Therefore there is a need for methods of reducing aggression in lactating piglets and improving feeding behavior to improve production efficiency and farm profitability, and to improve pig welfare.

SUMMARY OF THE INVENTION

One aspect of the present disclosure encompasses a composition for reducing aggression and improving feeding behavior in a suid. The composition comprises a combination of pheromonal agents, wherein the pheromonal agents comprise 3-methylindole (skatole) and myristic acid. The suid can be a lactating piglet or a weaned piglet. The composition can comprise skatole in an amount ranging from about 0.01 ppm to about 3,000 ppm of the composition. The composition can comprise myristic acid in an amount ranging from about 0.01 ppm to about 3,000 ppm of the composition. The ratio of skatole to myristic acid in the composition can range from about 4:1 to about 1:1.

The composition can also be formulated for addition to the suid environment. The composition can also be added to a feed composition. When added to a feed composition, the feed composition can comprise skatole in an amount ranging from about 1,600 ppm to about 2,000 ppm of the composition, and myristic acid in an amount ranging from about 700 ppm to about 1,100 ppm of the composition.

Another aspect of the present disclosure encompasses a method of reducing aggression and improving feeding behavior in a suid. The method comprises administering a pheromone composition to the suid, the composition comprising a combination of pheromonal agents, wherein the pheromonal agents comprise skatole and myristic acid.

The method can improve efficiency, growth performance, health, weight gain, welfare, and productivity of the suid.

The composition can be administered to a nursing piglet, or a weaned piglet. Further, the composition can be administered to the pig from birth until weaning, for 24 to 48 hours after weaning, or throughout lactation and for 24 to 48 hours after weaning.

The composition can be administered by inhalation and/or gustatory administration. In some aspects, the method comprises administering the pheromonal composition by adding the agents in a feed composition.

DETAILED DESCRIPTION

Figure 1A:
FIG. 1A depicts a photograph showing control litters with maternal feces.

The present disclosure is based in part on the surprising discovery of pheromonal agents capable of substantially reducing aggression among suids. The inventors have identified two pheromonal agents in maternal feces from lactating sows. When exposed to the pheromonal agents, aggressive behavior between suids is substantially reduced. For instance, piglets exposed to the agents spend significantly more time feeding when compared to piglets that were not exposed to the pheromonal agents. Advantageously, the pheromonal agents have also been found to be useful in improving reproductive and litter performance and yield of suids. Surprisingly, the beneficial effects of the pheromonal agents are only observed when the suids are exposed to a combination of both pheromonal agents. The beneficial effects are not observed when the suids are exposed to each of the single molecules.

Past work identified putative semiochemicals from the skin washings of a sow's udder. These molecules have variable effects on pigs. Most of these molecules are found in growing pig, pregnant sow and lactating sow secretions. Pregnant and lactating sows are fed different diets in different amounts and therefore, their odorous secretions are impacted by diet which was not controlled in earlier work. Conversely, the inventors fed the same pregnant and lactating sows the same diet and collected samples containing putative pheromones, and determined for the first time, that the lactating sow begins secreting high amounts of Skatole and Myristic acid only during lactation. Other organic molecules found in secretions/excretions of lactating sows that are also found in similar amounts in gestating sow secretions/excretions cannot be a lactation-maternal pheromone.

The suid can be a lactating piglet, a weaned piglet, or an adult sow or boar. In some aspects, the suid is a lactating female. In other aspects, the suid is a weaned piglet. In yet other aspects, the suid can be an adult sow. In other aspects, the suid is an adult boar.

I. Composition

The present invention encompasses a composition for reducing aggression, improving feeding behavior and welfare of the piglets, thereby improving efficiency, growth performance, and health of a suid. The composition comprises a combination of pheromonal agents, wherein the pheromonal agents comprise 3-methylindole (skatole) and myristic acid, and any salts and derivatives thereof. The chemical structures of skatole and myristic acid are shown below.

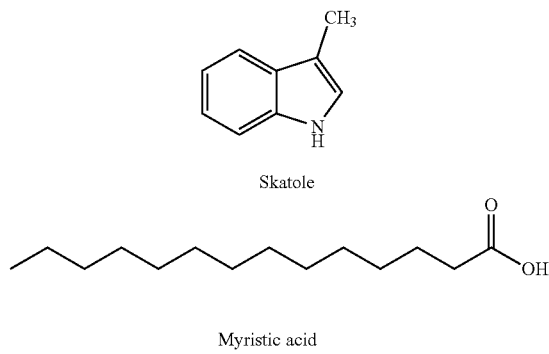

Skatole

Myristic acid

Skatole can be present in the pheromonal composition in an amount ranging from about 0.001 ppm to about 30,000 ppm, from about 0.005 ppm to about 10,000 ppm, or from about 0.01 ppm to about 5,000 ppm. In some aspects, skatole is present in the pheromonal composition in an amount ranging from about 0.01 ppm to about 3,000 ppm of the composition. The pheromonal composition can comprise skatole at a concentration ranging from about 0.01 to about 5 mg/ml, about 0.05 to about 2 mg/ml, about 0.1 to about 5 mg/ml, about 0.1 to about 1 mg/ml, or about 0.2 to about 0.4 mg/ml of skatole.

Myristic acid can be present in an amount ranging from about 0.001 ppm to about 30,000 ppm, from about 0.005 ppm to about 10,000 ppm, or from about 0.1 ppm to about 5,000 ppm. In some aspects, myristic acid is present in the pheromonal composition in an amount ranging from about 0.01 ppm to about 3,000 ppm of the composition. The pheromonal composition can comprise myristic acid at a concentration ranging from about 0.02 to about 10 mg/ml, about 0.1 to about 4 mg/ml, about 0.2 to about 10 mg/ml, about 0.2 to about 2 mg/ml, or about 0.4 to about 1 mg/ml of myristic acid.

Irrespective of the amount of skatole and myristic acid in the composition, the pheromonal agents can be present in the composition at a ratio of skatole to myristic acid ranging from about 10:1 to about 1:10, from about 8:1 to about 1:5, or from about 5:1 to about 1:2. In some aspects, the pheromonal agents are present in the composition at a ratio of skatole to myristic acid ranging from about 4:1 to about 1:1.

Exposing piglets to the pheromonal agents can be accomplished using any suitable method for delivering an effective amount of the composition to the olfactory and/or gustatory system of the piglets. Such methods can include, for example, placing or distributing the composition in the environment of the suid, either by premixing the pheromonal agents with the animal's feed or drinking water, by applying (e.g., spraying or wiping) the composition directly to surfaces in the living environment of the suid such as on a feeder in the environment of the suid, by using an automated sprayer, or by applying directly onto the suid, such as to its environment, or on its facial region, snout, or head. As such, the agents can be applied to a feed composition or premixing the agents with a feed composition. The composition can also be formulated for application to surfaces in the living environment of the suid such as a feeder in the environment of the suid or directly onto the suid or combinations thereof.

In some aspects, the pheromonal composition is formulated for application to surfaces in the living environment of the suid or directly onto the suid or combinations thereof. For example, compositions can be further prepared according to methods well known in the art into liquid formulations suitable for use in a pump spray, aerosol, gel, foam, cream, lotion, or diffuser. For instance, the pheromonal agents may be combined with one or more additional components such as solvents, propellants, surface-active agents, emulsifiers or thickeners, foaming agents, preservatives, and fragrances to prepare the various formulations.

In some aspects, the pheromonal composition is added to a feed composition. As such, an aspect of the instant disclosure the composition comprises a feed composition comprising the pheromonal agents. The pheromonal agents can be added to the feed composition by directly applying the agents to a feed composition, or by combining or formulating the agents with the feed composition. When the pheromonal composition is added to a feed composition, the feed composition comprises skatole in an amount ranging from about 0.01 ppm to about 30,000 ppm, from about 0.05 ppm to about 10,000 ppm, from about 0.1 ppm to about 5,000 ppm or from about 0.1 ppm to about 3,000 ppm of the composition. In some aspects, skatole is present in the pheromonal composition in an amount ranging from about 1,600 ppm to about 2,000 ppm of the composition. Further, when the pheromonal composition is added to a feed composition, the feed composition comprises myristic acid in an amount ranging from about 0.01 ppm to about 30,000 ppm, from about 0.05 ppm to about 10,000 ppm, from about 0.1 ppm to about 5,000 ppm or from about 0.1 ppm to about 3,000 ppm of the composition. In some aspects, myristic acid is present in the pheromonal composition in an amount ranging from about 700 ppm to about 1,100 ppm of the composition. Irrespective of the amount of skatole and myristic acid added to a feed composition, the pheromonal agents can be present in the feed composition at a ratio of skatole to myristic acid ranging from about 10:1 to about 1:10, from about 8:1 to about 1:5, or from about 5:1 to about 1:2. In some aspects, the pheromonal agents are present in the feed composition at a ratio of skatole to myristic acid ranging from about 4:1 to about 1:1.

The terms "feed", "food", "feed composition", and "feed supplement", are used herein interchangeably and may refer to any feed composition normally fed to an animal. Feed compositions normally fed to an animal are known in the art.

A feed composition may include one or more components of an animal feed. Non-limiting examples of feed matter or animal feed matter may include, without limitation: corn or a component of corn, such as, for example, corn meal, corn fiber, corn hulls, corn DDGS (distiller's dried grain with solubles), silage, ground corn, corn germ, corn gluten, corn oil, or any other portion of a corn plant; soy or a component of soy, such as, for example, soy oil, soy meal, soy hulls, soy silage, ground soy, or any other portion of a soy plant; wheat or any component of wheat, such as, for example, wheat meal, wheat fiber, wheat hulls, wheat chaff, ground wheat, wheat germ, or any other portion of a wheat plant; canola, such as, for example, canola oil, canola meal, canola protein, canola hulls, ground canola, or any other portion of a canola plant; sunflower or a component of a sunflower plant; sorghum or a component of a sorghum plant; sugar beet or a component of a sugar beet plant; cane sugar or a component of a sugarcane plant; barley or a component of a barley plant; palm oil, palm kernel or a component of a palm plant; glycerol; corn steep liquor; a waste stream from an agricultural processing facility; lecithin; rumen protected fats; molasses; soy molasses; flax; peanuts; peas; oats; grasses, such as orchard grass and fescue; fish meal, meat & bone meal; feather meal; and poultry byproduct meal; and alfalfa and/or clover used for silage or hay, and various combinations of any of the feed ingredients set forth herein, or other feed ingredients generally known in the art. As it will be recognized in the art, a feed composition may further be supplemented with amino acids, vitamins, minerals, and other feed additives such as other types of enzymes, organic acids, essential oils, probiotics, prebiotics, antioxidants, pigments, anti-caking agents, and the like, as described further below.

A feed composition may be formulated for administration to any animal subject. Suitable subjects include all mammals, avian species, and aquaculture. Non-limiting examples of food animals include poultry (e.g., chickens, including broilers, layers, and breeders, ducks, game hens, geese, guinea fowl/hens, quail, and turkeys), beef cattle, dairy cattle, veal, pigs, goats, sheep, bison, and fishes. Suitable companion animals include, but are not limited to, cats, dogs, horses, rabbits, rodents (e.g., mice, rats, hamsters, gerbils, and guinea pigs), hedgehogs, and ferrets. Examples of research animals include rodents, cats, dogs, rabbits, pigs, and non-human primates. Non-limiting examples of suitable zoo animals include non-human primates, lions, tigers, bears, elephants, giraffes, and the like.

According to various embodiments of the present invention, the feed may be in any suitable form known in the animal feed art, and may be a wet or dry component. For example, according to certain embodiments, the feed composition may be in a form selected from the group consisting of a complete feed, a feed supplement, a feed additive, a premix, a top-dress, a tub, a mineral, a meal, a block, a pellet, a mash, a liquid supplement, a drench, a bolus, a treat, and combinations of any thereof. Additionally, a feed sample may optionally be ground before preparing a feed composition.

The dietary supplements or feed compositions may optionally comprise at least one additional nutritive and/or pharmaceutical agent. For instance, the at least one additional nutritive and/or pharmaceutical agent may be selected from the group consisting of vitamin, mineral, amino acid, antioxidant, probiotic, essential fatty acid, and pharmaceutically acceptable excipient. The compositions may include one additional nutritive and/or pharmaceutical component or a combination of any of the foregoing additional components in varying amounts. Suitable examples of each additional component are detailed below.

a. Vitamins

Optionally, the dietary supplement of the invention may include one or more vitamins. Suitable vitamins for use in the dietary supplement include vitamin C, vitamin A, vitamin E, vitamin B12, vitamin K, riboflavin, niacin, vitamin D, vitamin B6, folic acid, pyridoxine, thiamine, pantothenic acid, and biotin. The form of the vitamin may include salts of the vitamin, derivatives of the vitamin, compounds having the same or similar activity of a vitamin, and metabolites of a vitamin.

The dietary supplement may include one or more forms of an effective amount of any of the vitamins described herein or otherwise known in the art. Exemplary vitamins include vitamin K, vitamin D, vitamin C, and biotin. An "effective amount" of a vitamin typically quantifies an amount at least about 10% of the United States Recommended Daily Allowance ("RDA") of that particular vitamin for a subject. It is contemplated, however, that amounts of certain vitamins exceeding the RDA may be beneficial for certain subjects. For example, the amount of a given vitamin may exceed the applicable RDA by 100%, 200%, 300%, 400%, 500% or more.

b. Minerals

In addition to the metal chelates or metal salts described in Section Ia, the dietary supplement may include one or more minerals or mineral sources. Non-limiting examples of minerals include, without limitation, calcium, iron, chromium, copper, iodine, zinc, magnesium, manganese, molybdenum, phosphorus, potassium, and selenium. Suitable forms of any of the foregoing minerals include soluble mineral salts, slightly soluble mineral salts, insoluble mineral salts, chelated minerals, mineral complexes, non-reactive minerals such as carbonyl minerals, and reduced minerals, and combinations thereof.

In an exemplary embodiment, the mineral may be a form of calcium. Suitable forms of calcium include calcium alpha-ketoglutarate, calcium acetate, calcium alginate, calcium ascorbate, calcium aspartate, calcium caprylate, calcium carbonate, calcium chelates, calcium chloride, calcium citrate, calcium citrate malate, calcium formate, calcium glubionate, calcium glucoheptonate, calcium gluconate, calcium glutarate, calcium glycerophosphate, calcium lactate, calcium lysinate, calcium malate, calcium orotate, calcium oxalate, calcium oxide, calcium pantothenate, calcium phosphate, calcium pyrophosphate, calcium succinate, calcium sulfate, calcium undecylenate, coral calcium, dicalcium citrate, dicalcium malate, dihydroxycalcium malate, dicalcium phosphate, and tricalcium phosphate.

Generally speaking, the dietary supplement may include one or more forms of an effective amount of any of the minerals described herein or otherwise known in the art. An "effective amount" of a mineral typically quantifies an amount at least about 10% of the United States Recommended Daily Allowance ("RDA") of that particular mineral for a subject. It is contemplated, however, that amounts of certain minerals exceeding the RDA may be beneficial for certain subjects. For example, the amount of a given mineral may exceed the applicable RDA by 100%, 200%, 300%, 400%, 500% or more. Typically, the amount of mineral included in the dietary supplement may range from about 1 mg to about 1500 mg, about 5 mg to about 500 mg, or from about 50 mg to about 500 mg per dosage.

c. Essential Fatty Acids

Optionally, the dietary supplement may include a source of an essential fatty acid. The essential fatty acid may be isolated or it may be an oil source or fat source that contains an essential fatty acid. In one embodiment, the essential fatty acid may be a polyunsaturated fatty acid (PUFA), which has at least two carbon-carbon double bonds generally in the cis-configuration. The PUFA may be a long chain fatty acid having at least 18 carbons atoms. The PUFA may be an omega-3 fatty acid in which the first double bond occurs in the third carbon-carbon bond from the methyl end of the carbon chain (i.e., opposite the carboxyl acid group). Examples of omega-3 fatty acids include alpha-linolenic acid (18:3, ALA), stearidonic acid (18:4), eicosatetraenoic acid (20:4), eicosapentaenoic acid (20:5; EPA), docosatetraenoic acid (22:4), n-3 docosapentaenoic acid (22:5; n-3DPA), and docosahexaenoic acid (22:6; DHA). The PUFA may also be an omega-5 fatty acid, in which the first double bond occurs in the fifth carbon-carbon bond from the methyl end. Exemplary omega-5 fatty acids include myristoleic acid (14:1), myristoleic acid esters, and cetyl myristoleate. The PUFA may also be an omega-6 fatty acid, in which the first double bond occurs in the sixth carbon-carbon bond from the methyl end. Examples of omega-6 fatty acids include linoleic acid (18:2), gamma-linolenic acid (18:3), eicosadienoic acid (20:2), dihomo-gamma-linolenic acid (20:3), arachidonic acid (20:4), docosadienoic acid (22:2), adrenic acid (22:4), and n-6 docosapentaenoic acid (22:5). The fatty acid may also be an omega-9 fatty acid, such as oleic acid (18:1), eicosenoic acid (20:1), mead acid (20:3), erucic acid (22:1), and nervonic acid (24:1).

In another embodiment, the essential fatty acid source may be a seafood-derived oil. The seafood may be a vertebrate fish or a marine organism, such that the oil may be fish oil or marine oil. The long chain (20C, 22C) omega-3 and omega-6 fatty acids are found in seafood. The ratio of omega-3 to omega-6 fatty acids in seafood ranges from about 8:1 to 20:1. Seafood from which oil rich in omega-3 fatty acids may be derived includes, but is not limited to, abalone scallops, albacore tuna, anchovies, catfish, clams, cod, gem fish, herring, lake trout, mackerel, menhaden, orange roughy, salmon, sardines, sea mullet, sea perch, shark, shrimp, squid, trout, and tuna.

In yet another embodiment, the essential fatty acid source may be a plant-derived oil, or they may be chemically synthesized. Plant and vegetable oils are rich in omega-6 fatty acids. Some plant-derived oils, such as flaxseed oil, are especially rich in omega-3 fatty acids. Plant or vegetable oils are generally extracted from the seeds of a plant, but may also be extracted from other parts of the plant. Plant or vegetable oils that are commonly used for cooking or flavoring include, but are not limited to, acai oil, almond oil, amaranth oil, apricot seed oil, argan oil, avocado seed oil, babassu oil, ben oil, blackcurrant seed oil, Borneo tallow nut oil, borage seed oil, buffalo gourd oil, canola oil, carob pod oil, cashew oil, castor oil, coconut oil, coriander seed oil, corn oil, cottonseed oil, evening primrose oil, false flax oil, flax seed oil, grapeseed oil, hazelnut oil, hemp seed oil, kapok seed oil, lallemantia oil, linseed oil, macadamia oil, meadowfoam seed oil, mustard seed oil, okra seed oil, olive oil, palm oil, palm kernel oil, peanut oil, pecan oil, pequi oil, perilla seed oil, pine nut oil, pistachio oil, poppy seed oil, prune kernel oil, pumpkin seed oil, quinoa oil, ramtil oil, rice bran oil, safflower oil, sesame oil, soybean oil, sunflower oil, tea oil, thistle oil, walnut oil, or wheat germ oil. The plant derived oil may also be hydrogenated or partially hydrogenated.

In still a further embodiment, the essential fatty acid source may be an algae-derived oil. Commercially available algae-derived oils include those from *Crypthecodinium cohnii* and *Schizochytrium* sp. Other suitable species of algae, from which oil is extracted, include Aphanizomenon flos-aquae, *Bacilliarophy* sp., *Botryococcus braunii*, *Chlorophyceae* sp., *Dunaliella tertiolecta*, *Euglena gracilis*, *Isochrysis galbana*, *Nannochloropsis salina*, *Nannochloris* sp., *Neochloris oleoabundans*, *Phaeodactylum tricornutum*, *Pleurochrysis carterae*, *Prymnesium parvum*, *Scenedesmus dimorphus*, *Spirulina* sp., and *Tetraselmis chui*.

d. Amino Acids

The dietary supplement may optionally include from one to several amino acids. Suitable amino acids include alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine or their hydroxy analogs. In certain embodiments, the amino acid will be selected from the essential amino acids. An essential amino acid is generally described as one that cannot be synthesized de novo by the organism, and therefore, must be provided in the diet. By way of non-limiting example, the essential amino acids for humans include: L-histidine, L-isoleucine, L-leucine, L-lysine, L-methionine, L-phenylalanine, L-valine and L-threonine.

e. Antioxidants

The dietary supplement may include one or more suitable antioxidants. As will be appreciated by a skilled artisan, the suitability of a given antioxidant will vary depending upon the species to which the dietary supplement will be administered. Non-limiting examples of antioxidants include ascorbic acid and its salts, ascorbyl palmitate, ascorbyl stearate, anoxomer, N-acetylcysteine, benzyl isothiocyanate, o-, m- or p-amino benzoic acid (o is anthranilic acid, p is PABA), butylated hydroxyanisole (BHA), butylated hydroxytoluene (BHT), caffeic acid, canthaxantin, alpha-carotene, beta-carotene, beta-caraotene, beta-apo-carotenoic acid, carnosol, carvacrol, catechins, cetyl gallate, chlorogenic acid, citric acid and its salts, p-coumaric acid, curcurin, 3,4-dihydroxybenzoic acid, N,N'-diphenyl-p-phenylenediamine (DPPD), dilauryl thiodipropionate, distearyl thiodipropionate, 2,6-di-tert-butylphenol, dodecyl gallate, edetic acid, ellagic acid, erythorbic acid, sodium erythorbate, esculetin, esculin, 6-ethoxy-1,2-dihydro-2,2,4-trimethylquinoline, ethyl gallate, ethyl maltol, ethylenediaminetetraacetic acid (EDTA), eugenol, ferulic acid, flavonoids, flavones (e.g., apigenin, chrysin, luteolin), flavonols (e.g., datiscetin, myricetin, daemfero), flavanones, fraxetin, fumaric acid, gallic acid, gentian extract, gluconic acid, glycine, gum guaiacum, hesperetin, alpha-hydroxybenzyl phosphinic acid, hydroxycinammic acid, hydroxyglutaric acid, hydroquinone, N-hydroxysuccinic acid, hydroxytyrosol, hydroxyurea, lactic acid and its salts, lecithin, lecithin citrate; R-alpha-lipoic acid, lutein, lycopene, malic acid, maltol, 5-methoxy tryptamine, methyl gallate, monoglyceride citrate; monoisopropyl citrate; morin, beta-naphthoflavone, nordihydroguaiaretic acid (NDGA), octyl gallate, oxalic acid, palm ityl citrate, phenothiazine, phosphatidylcholine, phosphoric acid, phosphates, phytic acid, phytylubichromel, propyl gallate, polyphosphates, quercetin, trans-resveratrol, rosmarinic acid, sesamol, silymarin, sinapic acid, succinic acid, stearyl citrate, syringic acid, tartaric acid, thymol, tocopherols (i.e., alpha-, beta-, gamma- and delta-tocopherol), tocotrienols (i.e., alpha-, beta-, gamma- and delta-tocotrienols), tyrosol, vanilic acid, 2,6-di-tert-butyl-4-hydroxymethylphenol (i.e., lonox 100), 2,4-(tris-3',5'-bi-tert-butyl-4'-hydroxybenzyl)-mesitylene (i.e., lonox 330), 2,4,5-trihydroxybutyrophenone, ubiquinone, tertiary butyl hydroquinone (TBHQ), thiodipropionic acid, trihydroxy butyrophenone, tryptamine, tyramine, uric acid, vitamin K and derivates, vitamin Q10, zeaxanthin, or combinations thereof.

Natural antioxidants that may be included in the dietary supplement include, but are not limited to, apple peel extract, blueberry extract, carrot juice powder, clove extract, coffeeberry, coffee bean extract, cranberry extract, eucalyptus extract, ginger powder, grape seed extract, green tea, olive leaf, parsley extract, peppermint, pimento extract, pomace, pomegranate extract, rice bran extract, rosehips, rosemary extract, sage extract, tart cherry extract, tomato extract, tumeric, and wheat germ oil.

f. Anti-Inflammatory Agents

The dietary supplement may optionally include at least one anti-inflammatory agent. In one embodiment, the anti-inflammatory agent may be a synthetic steroid or non-steroidal anti-inflammatory drug (NSAID) such as acetylsalicylic acid, dichlophenac, indomethacin, oxamethacin, ibuprofen, indoprofen, naproxen, ketoprofen, mefamanic acid, metamizole, piroxicam, and celecoxib. In an alternate embodiment, the anti-inflammatory agent may be a prohormone that modulates inflammatory processes. Suitable prohormones having this property include prohormone convertase 1, proopiomelanocortin, prohormone B-type natriuretic peptide, SMR1 prohormone, and the like. In another embodiment, the anti-inflammatory agent may be an enzyme having anti-inflammatory effects. Examples of anti-inflammatory enzymes include bromelain, papain, serrapeptidase, and proteolytic enzymes such as pancreatin (a mixture of tyrpsin, amylase and lipase).

In still another embodiment, the anti-inflammatory agent may be a peptide with anti-inflammatory effects. For example, the peptide may be an inhibitor of phospholipase A2, such as antiflammin-1, a peptide that corresponds to amino acid residues 246-254 of lipocortin; antiflammin-2, a peptide that corresponds to amino acid residues 39-47 of uteroglobin; S7 peptide, which inhibits the interaction between interleukin 6 and interleukin 6 receptor; RP1, a prenyl protein inhibitor; and similar peptides. Alternatively, the anti-inflammatory peptide may be cortistatin, a cyclic neuropeptide related to somatostatin, or peptides that correspond to an N-terminal fragment of SV-IV protein, a conserved region of E-, L-, and P-selectins, and the like. Other suitable anti-inflammatory preparations include collagen hydrolysates and milk micronutrient concentrates (e.g., MicroLactin® available from Stolle Milk Biologics, Inc., Cincinnati, OH), as well as milk protein hydrolysates, casein hydrolysates, whey protein hydrolysates, and plant protein hydrolysates.

In a further embodiment, the anti-inflammatory agent may be a probiotic that has been shown to modulate inflammation. Suitable immunomodulatory probiotics include lactic acid bacteria such as acidophilli, lactobacilli, and bifidophilli. In yet another embodiment, the anti-inflammatory agent may be a plant extract having anti-inflammatory properties. Non-limiting examples of suitable plant extracts with anti-inflammatory benefits include blueberries, boswella, black catechu and Chinese skullcap, celery seed, chamomile, cherries, devils claw, eucalyptus, evening primrose, ginger, hawthorne berries, horsetail, Kalopanax pictus bark, licorice root, tumeric, white wallow, willow bark, and yucca.

g. Probiotics

Probiotics and prebiotics may include yeast and bacteria that help establish an immune protective rumen or gut microflora as well as small oligosaccharides. By way of non-limiting example, yeast-derived probiotics and prebiotics include yeast cell wall derived components such as β-glucans, arabinoxylan isomaltose, agarooligosaccharides, lactosucrose, cyclodextrins, lactose, fructooligosaccharides, lam inariheptaose, lactulose, β-galactooligosaccharides, mannanoligosaccharides, raffinose, stachyose, oligofructose, glucosyl sucrose, sucrose thermal oligosaccharide, isomalturose, caramel, inulin, and xylooligosaccharides. In an exemplary embodiment, the yeast-derived agent may be β-glucans and/or mannanoligosaccharides. Sources for yeast cell wall derived components include *Saccharomyces bisporus, Saccharomyces boulardii, Saccharomyces cerevisiae, Saccharomyces capsularis, Saccharomyces delbrueckii, Saccharomyces fermentati, Saccharomyces lugwigii, Saccharomyces microellipsoides, Saccharomyces pastorianus, Saccharomyces rosei, Candida albicans, Candida cloaceae, Candida tropicalis, Candida utilis, Geotrichum candidum, Hansenula americana, Hansenula anomala, Hansenula wingei,* and *Aspergillus oryzae.*

Probiotics and prebiotics may also include bacteria cell wall derived agents such as peptidoglycan and other components derived from gram-positive bacteria with a high content of peptidoglycan. Exemplary gram-positive bacteria include *Lactobacillus acidophilus, Bifedobact thermophilum, Bifedobat longhum, Streptococcus faecium, Bacillus pumilus, Bacillus subtilis, Bacillus licheniformis, Lactobacillus acidophilus, Lactobacillus casei, Enterococcus faecium, Bifidobacterium bifidium, Propionibacterium acidipropionici, Propionibacteriium freudenreichii,* and *Bifidobacterium pscudolongum.* h. Herbals

Suitable herbals and herbal derivatives, as used herein, refer to herbal extracts, and substances derived from plants and plant parts, such as leaves, flowers and roots, without limitation. Non-limiting exemplary herbals and herbal derivatives include agrimony, alfalfa, aloe vera, amaranth, angelica, anise, barberry, basil, bayberry, bee pollen, birch, bistort, blackberry, black cohosh, black walnut, blessed thistle, blue cohosh, blue vervain, boneset, borage, buchu, buckthorn, bugleweed, burdock, capsicum, cayenne, caraway, cascara sagrada, catnip, celery, centaury, chamomile, chaparral, chickweed, chicory, chinchona, cloves, coltsfoot, comfrey, cornsilk, couch grass, cramp bark, culver's root, cyani, cornflower, damiana, dandelion, devils claw, dong quai, echinacea, elecampane, ephedra, eucalyptus, evening primrose, eyebright, false unicorn, fennel, fenugreek, figwort, flaxseed, garlic, gentian, ginger, ginseng, golden seal, gotu kola, gum weed, hawthorn, hops, horehound, horseradish, horsetail, hoshouwu, hydrangea, hyssop, iceland moss, irish moss, jojoba, juniper, kelp, lady's slipper, lemon grass, licorice, lobelia, mandrake, marigold, marjoram, marshmallow, mistletoe, mullein, mustard, myrrh, nettle, oatstraw, oregon grape, papaya, parsley, passion flower, peach, pennyroyal, peppermint, periwinkle, plantain, pleurisy root, pokeweed, prickly ash, psyllium, quassia, queen of the meadow, red clover, red raspberry, redmond clay, rhubarb, rose hips, rosemary, rue, safflower, saffron, sage, St. John's wort, sarsaparilla, sassafras, saw palmetto, skullcap, senega, senna, shepherd's purse, slippery elm, spearmint, spikenard, squawvine, stillingia, strawberry, taheebo, thyme, uva ursi, valerian, violet, watercress, white oak bark, white pine bark, wild cherry, wild lettuce, wild yam, willow, wintergreen, witch hazel, wood betony, wormwood, yarrow, yellow dock, yerba santa, yucca and combinations thereof.

i. Pigments

Suitable non-limiting pigments include actinioerythrin, alizarin, alloxanthin, β-apo-2'-carotenal, apo-2-lycopenal, apo-6'-lycopenal, astacein, astaxanthin, azafrinaldehyde, aacterioruberin, aixin, α-carotine, β-carotine, γ-carotine, β-carotenone, canthaxanthin, capsanthin, capsorubin, citranaxanthin, citroxanthin, crocetin, crocetinsemialdehyde, crocin, crustaxanthin, cryptocapsin, α-cryptoxanthin, β-cryptoxanthin, cryptomonaxanthin, cynthiaxanthin, decaprenoxanthin, dehydroadonirubin, diadinoxanthin, 1,4-diamino-2,3-dihydroanthraquinone, 1,4-dihydroxyanthraquinone, 2,2'-Diketospirilloxanthin, eschscholtzxanthin, eschscholtzxanthone, flexixanthin, foliachrome, fucoxanthin, gazaniaxanthin, hexahydrolycopene, hopkinsiaxanthin, hydroxyspheriodenone, isofucoxanthin, loroxanthin, lutein, luteoxanthin, lycopene, lycopersene, lycoxanthin, morindone, mutatoxanthin, neochrome, neoxanthin, nonaprenoxanthin, OH-Chlorobactene, okenone, oscillaxanthin, paracentrone, pectenolone, pectenoxanthin, peridinin, phleixanthophyll, phoeniconone, phoenicopterone, phoenicoxanthin, physalien, phytofluene, pyrrhoxanthininol, quinones, rhodopin, rhodopinal, rhodopinol, rhodovibrin, rhodoxanthin, rubixanthone, saproxanthin, semi-a-carotenone, sem i-β-carotenone, sintaxanthin, siphonaxanthin, siphonein, spheroidene, tangeraxanthin, torularhodin, torularhodin methyl ester, torularhodinaldehyde, torulene, 1,2,4-trihydroxyanthraquinone, triphasiaxanthin, trollichrome, vaucheriaxanthin, violaxanthin, wamingone, xanthin, zeaxanthin, α-zeacarotene and combinations thereof.

j. Pharmaceutical Agents

Suitable non-limiting pharmaceutically acceptable agents include an acid/alkaline-labile drug, a pH dependent drug, or a drug that is a weak acid or a weak base. Examples of acid-labile drugs include statins (e.g., pravastatin, fluvastatin and atorvastatin), antiobiotics (e.g., penicillin G, ampicillin, streptomycin, erythromycin, clarithromycin and azithromycin), nucleoside analogs (e.g., dideoxyinosine (ddI or didanosine), dideoxyadenosine (ddA), dideoxycytosine (ddC)), salicylates (e.g., aspirin), digoxin, bupropion, pancreatin, midazolam, and methadone. Drugs that are only soluble at acid pH include nifedipine, emonapride, nicardipine, amosulalol, noscapine, propafenone, quinine, dipyridamole, josamycin, dilevalol, labetalol, enisoprost, and metronidazole. Drugs that are weak acids include phenobarbital, phenytoin, zidovudine (AZT), salicylates (e.g., aspirin), propionic acid compounds (e.g., ibuprofen), indole derivatives (e.g., indomethacin), fenamate compounds (e.g., meclofenamic acid), pyrrolealkanoic acid compounds (e.g., tolmetin), cephalosporins (e.g., cephalothin, cephalaxin, cefazolin, cephradine, cephapirin, cefamandole, and cefoxitin), 6-fluoroquinolones, and prostaglandins. Drugs that are weak bases include adrenergic agents (e.g., ephedrine, desoxyephedrine, phenylephrine, epinephrine, salbutamol, and terbutaline), cholinergic agents (e.g., physostigmine and neostigmine), antispasmodic agents (e.g., atropine, methantheline, and papaverine), curariform agents (e.g., chlorisondamine), tranquilizers and muscle relaxants (e.g., fluphenazine, thioridazine, trifluoperazine, chlorpromazine, and triflupromazine), antidepressants (e.g., am itriptyline and nortriptyline), antihistamines (e.g., diphenhydramine, chlorpheniramine, dimenhydrinate, tripelennamine, perphenazine, chlorprophenazine, and chlorprophenpyridamine), cardioactive agents (e.g., verapamil, diltiazem, gallapomil, cinnarizine, propranolol, metoprolol and nadolol), antimalarials (e.g., chloroquine), analgesics (e.g., propoxyphene and meperidine), antifungal agents (e.g., ketoconazole and itraconazole), antimicrobial agents (e.g., cefpodoxime, proxetil, and enoxacin), caffeine, theophylline, and morphine. In another embodiment, the drug may be a biphosphonate or another drug used to treat osteoporosis. Non-limiting examples of a biphosphonate include alendronate, ibandronate, risedronate, zoledronate, pamidronate, neridronate, olpadronate, etidronate, clodronate, and tiludronate. Other suitable drugs include estrogen, selective estrogen receptor modulators (SERMs), and parathyroid hormone (PTH) drugs. In yet another embodiment, the drug may be an antibacterial agent. Suitable antibiotics include aminoglycosides (e.g., amikacin, gentamicin, kanamycin, neomycin, netilmicin, streptomycin, and tobramycin), carbecephems (e.g., loracarbef), a carbapenem (e.g., certapenem, imipenem, and meropenem), cephalosporins (e.g., cefadroxil cefazolin, cephalexin, cefaclor, cefamandole, cephalexin, cefoxitin, cefprozil, cefuroxime, cefixime, cefdinir, cefditoren, cefoperazone, cefotaxime, cefpodoxime, ceftazidime, ceftibuten, ceftizoxime, and ceftriaxone), macrolides (e.g., azithromycin, clarithromycin, dirithromycin, erythromycin, and troleandomycin), monobactam, penicillins (e.g., amoxicillin, ampicillin, carbenicillin, cloxacillin, dicloxacillin, nafcillin, oxacillin, penicillin G, penicillin V, piperacillin, and ticarcillin), polypeptides (e.g., bacitracin, colistin, and polymyxin B), quinolones (e.g., ciprofloxacin, enoxacin, gatifloxacin, levofloxacin, lomefloxacin, moxifloxacin, norfloxacin, ofloxacin, and trovafloxacin), sulfonamides (e.g., mafenide, sulfacetamide, sulfamethizole, sulfasalazine, sulfisoxazole, and trimethoprim-sulfamethoxazole), and tetracyclines (e.g., demeclocycline, doxycycline, minocycline, and oxytetracycline). In an alternate embodiment, the drug may be an antiviral protease inhibitor (e.g., amprenavir, fosamprenavir, indinavir, lopinavir/ritonavir, ritonavir, saquinavir, and nelfinavir). In still another embodiment, the drug may be a cardiovascular drug. Examples of suitable cardiovascular agents include cardiotonic agents (e.g., digitalis (digoxin), ubidecarenone, and dopamine), vasodilating agents (e.g., nitroglycerin, captopril, dihydralazine, diltiazem, and isosorbide dinitrate), antihypertensive agents (e.g., alpha-methyldopa, chlortalidone, reserpine, syrosingopine, rescinnamine, prazosin, phentolamine, felodipine, propanolol, pindolol, labetalol, clonidine, captopril, enalapril, and lisonopril), beta blockers (e.g., levobunolol, pindolol, timolol maleate, bisoprolol, carvedilol, and butoxamine), alpha blockers (e.g., doxazosin, prazosin, phenoxybenzamine, phentolamine, tamsulosin, alfuzosin, and terazosin), calcium channel blockers (e.g., amlodipine, felodipine, nicardipine, nifedipine, nimodipine, nisoldipine, nitrendipine, lacidipine, lercanidipine, verapamil, gallopamil, and diltiazem), and anticlot agents (e.g., dipyrimadole).

k. Excipients

A variety of commonly used excipients in dietary supplement formulations may be selected on the basis of compatibility with the active ingredients. Non-limiting examples of suitable excipients include an agent selected from the group consisting of non-effervescent disintegrants, a coloring agent, a flavor-modifying agent, an oral dispersing agent, a stabilizer, a preservative, a diluent, a compaction agent, a lubricant, a filler, a binder, taste-masking agents, an effervescent disintegration agent, and combinations of any of these agents.

In one embodiment, the excipient is a binder. Suitable binders include starches, pregelatinized starches, gelatin, polyvinylpyrolidone, cellulose, methylcellulose, sodium carboxymethylcellulose, ethylcellulose, polyacrylam ides, polyvinyloxoazolidone, polyvinylalcohols, $C_{12}$-$C_{18}$ fatty acid alcohol, polyethylene glycol, polyols, saccharides, oligosaccharides, polypeptides, oligopeptides, and combinations thereof. The polypeptide may be any arrangement of amino acids ranging from about 100 to about 300,000 daltons.

In another embodiment, the excipient may be a filler. Suitable fillers include carbohydrates, inorganic compounds, and polyvinylpirrolydone. By way of non-limiting example, the filler may be calcium sulfate, both di- and tri-basic, starch, calcium carbonate, magnesium carbonate, microcrystalline cellulose, dibasic calcium phosphate, magnesium carbonate, magnesium oxide, calcium silicate, talc, modified starches, lactose, sucrose, mannitol, and sorbitol.

The excipient may comprise a non-effervescent disintegrant. Suitable examples of non-effervescent disintegrants include starches such as corn starch, potato starch, pregelatinized and modified starches thereof, sweeteners, clays, such as bentonite, micro-crystalline cellulose, alginates, sodium starch glycolate, gums such as agar, guar, locust bean, karaya, pecitin, and tragacanth.

In another embodiment, the excipient may be an effervescent disintegrant. By way of non-limiting example, suitable effervescent disintegrants include sodium bicarbonate in combination with citric acid and sodium bicarbonate in combination with tartaric acid.

The excipient may comprise a preservative. Suitable examples of preservatives include antioxidants, such as a-tocopherol or ascorbate, and antimicrobials, such as parabens, chlorobutanol or phenol.

In another embodiment, the excipient may include a diluent. Diluents suitable for use include pharmaceutically acceptable saccharide such as sucrose, dextrose, lactose, microcrystalline cellulose, fructose, xylitol, and sorbitol; polyhydric alcohols; a starch; pre-manufactured direct compression diluents; and mixtures of any of the foregoing.

The excipient may include flavors. Flavors incorporated into the outer layer may be chosen from synthetic flavor oils and flavoring aromatics and/or natural oils, extracts from plants, leaves, flowers, fruits, and combinations thereof. By way of example, these may include cinnamon oils, oil of wintergreen, peppermint oils, clover oil, hay oil, anise oil, eucalyptus, vanilla, citrus oil, such as lemon oil, orange oil, grape and grapefruit oil, fruit essences including apple, peach, pear, strawberry, raspberry, cherry, plum, pineapple, and apricot.

In another embodiment, the excipient may include a sweetener. By way of non-limiting example, the sweetener may be selected from glucose (corn syrup), dextrose, invert sugar, fructose, and mixtures thereof (when not used as a carrier); saccharin and its various salts such as the sodium salt; dipeptide sweeteners such as aspartame; dihydrochalcone compounds, glycyrrhizin; Stevia Rebaudiana (Stevioside); chloro derivatives of sucrose such as sucralose; sugar alcohols such as sorbitol, mannitol, sylitol, and the like.

In another embodiment, the excipient may be a lubricant. Suitable non-limiting examples of lubricants include magnesium stearate, calcium stearate, zinc stearate, hydrogenated vegetable oils, sterotex, polyoxyethylene monostearate, talc, polyethyleneglycol, sodium benzoate, sodium lauryl sulfate, magnesium lauryl sulfate, and light mineral oil.

The excipient may be a dispersion enhancer. Suitable dispersants may include starch, alginic acid, polyvinylpyrrolidones, guar gum, kaolin, bentonite, purified wood cellulose, sodium starch glycolate, isoamorphous silicate, and microcrystalline cellulose as high HLB emulsifier surfactants.

Depending upon the embodiment, it may be desirable to provide a coloring agent in the outer layer. Suitable color additives include food, drug and cosmetic colors (FD&C), drug and cosmetic colors (D&C), or external drug and cosmetic colors (Ext. D&C). These colors or dyes, along with their corresponding lakes, and certain natural and derived colorants, may be suitable for use in the present invention depending on the embodiment.

The excipient may include a taste-masking agent. Taste-masking materials include, e.g., cellulose hydroxypropyl ethers (HPC) such as Klucel®, Nisswo HPC and PrimaFlo HP22; low-substituted hydroxypropyl ethers (L-HPC); cellulose hydroxypropyl methyl ethers (HPMC) such as Seppifilm-LC, Pharmacoat®, Metolose SR, Opadry YS, PrimaFlo, MP3295A, Benecel MP824, and Benecel MP843; methylcellulose polymers such as Methocel® and Metolose®; Ethylcelluloses (EC) and mixtures thereof such as E461, Ethocel®, Aqualon®-EC, Surelease; Polyvinyl alcohol (PVA) such as Opadry AMB; hydroxyethylcelluloses such as Natrosol®; carboxymethylcelluloses and salts of carboxymethylcelluloses (CMC) such as Aualon®-CMC; polyvinyl alcohol and polyethylene glycol co-polymers such as Kollicoat IR®; monoglycerides (Myverol), triglycerides (KLX), polyethylene glycols, modified food starch, acrylic polymers and mixtures of acrylic polymers with cellulose ethers such as Eudragit® EPO, Eudragit® RD100, and Eudragit® E100; cellulose acetate phthalate; sepifilms such as mixtures of HPMC and stearic acid, cyclodextrins, and mixtures of these materials. In other embodiments, additional taste-masking materials contemplated are those described in U.S. Pat. Nos. 4,851,226; 5,075,114; and 5,876,759, each of which is hereby incorporated by reference in its entirety.

In various embodiments, the excipient may include a pH modifier. In certain embodiments, the pH modifier may include sodium carbonate or sodium bicarbonate.

The dietary supplement or feed compositions detailed herein may be manufactured in one or several dosage forms. In an exemplary embodiment, the dosage form will be an oral dosage form. Suitable oral dosage forms may include a tablet, for example a suspension tablet, a chewable tablet, an effervescent tablet or caplet; a pill; a powder, such as a sterile packaged powder, a dispensable powder, and an effervescent powder; a capsule including both soft or hard gelatin capsules or non-animal derived polymers, such as hydroxypropyl methylcellulose capsules (i.e., HPMC) or pullulan; a lozenge; a sachet; a sprinkle; a reconstitutable powder or shake; a troche; pellets; granules; liquids; lick blocks; suspensions; emulsions; or semisolids and gels. Alternatively, the dietary supplement may be incorporated in a food product or powder for mixing with a liquid, or administered orally after only mixing with a non-foodstuff liquid. As will be appreciated by a skilled artisan, the dietary supplements, in addition to being suitable for administration in multiple dosage forms, may also be administered with various dosage regimens. Additionally, the antimicrobial clay may simply be added to any dosage form of a dietary supplement or feed composition.

The amount and types of ingredients (i.e., metal chelate, chondroprotective agents, vitamin, mineral, amino acid, antioxidant, yeast culture, and essential fatty acid), and other excipients useful in each of these dosage forms, are described throughout the specification and examples. It should be recognized that where a combination of ingredients and/or excipients, including specific amounts of these components, is described with one dosage form that the same combination could be used for any other suitable dosage form. Moreover, it should be understood that one of skill in the art would, with the teachings found within this application, be able to make any of the dosage forms listed above by combining the amounts and types of ingredients administered as a combination in a single dosage form or separate dosage forms and administered together as described in the different sections of the specification.

The dietary supplements of the present invention can be manufactured by conventional pharmacological techniques. Conventional pharmacological techniques include, e.g., one or a combination of methods: (1) dry mixing; (2) direct compression; (3) milling; (4) dry or non-aqueous granulation; (5) wet granulation; or (6) fusion. See, e.g., Lachman et al., The Theory and Practice of Industrial Pharmacy (1986). Other methods include, e.g., prilling, spray drying, pan coating, melt granulation, granulation, wurster coating, tangential coating, top spraying, extruding, coacervation and the like.

II. Administration

One aspect of the present disclosure encompasses a method of reducing aggression and improving feeding behavior in a pig by administering a pheromone composition to the suid. The composition comprises a combination of skatole and myristic acid and can be as described in Section I above. The suid can be a nursing piglet or a weaned piglet or an older pig.

The animal can be exposed to an effective amount of skatole and myristic acid through inhalation and/or ingestion of the pheromonal agents over a period of time sufficient to effect a modification of the aggressive behavior previously observed. Typically, depending on the chosen route of administration (e.g., adding the agents to a feed composition or incorporating the agents into a spray formulation, etc.), the particular animal, the age of the animal, or other situations, the exposure of the pheromone composition to the animal will be over a period of at least one second, but can also be for a period of at least one hour, for a period of between one hour and five hours, for a period of between six hours and ten hours, for a period of at least one day, for a period of at least one week, for a period of between one week and four weeks, for a period of at least one month, or for any period of time as may be needed to achieve a satisfactory behavioral effect. A suid may be exposed to the agents during lactation, after weaning, during adulthood, or any combination and variations thereof. Additionally, suids may be exposed to the agents when a new animal is added into an established group of animals for at least the initial introductory period, until aggressive behavior is reduced.

In some aspects, the suid is exposed to the agents throughout the life of the suid. In other aspects, the suid is exposed to the agents during lactation. In one alternative of the aspect, the lactating suid is exposed to the agents throughout lactation. In other aspects, the suid is exposed to the agents at weaning. For instance, a weaned piglet can be exposed to the agents for 1, 2, 3, 4, 5, 6, 7 days or longer, or until the weaned suid is an adult. In one aspect, the suid is exposed to the agents for about 24 to about 48 hours at weaning. In another aspect, the suid is exposed to the agents throughout lactation and for about 24 to about 48 hours at weaning.

Administration of the composition to a subject suid is typically accomplished through any method allowing for delivery of an effective amount of the composition to the olfactory and/or gustatory system for an effective period of time. Such methods of administration include, for example, placing or distributing the composition in the environment of the suid, either by including in the animal's feed or drinking water, by applying (e.g., spraying or wiping) the composition to surfaces in the living environment of the suid, or by applying directly onto the suid, such as to its facial region, snout, or head. Further, the pheromonal composition can be administered to the suid using a combination of these methods.

In some aspects, the pheromonal composition is administered by adding or formulating the composition with a feed composition. Feed compositions and feed compositions having the pheromonal composition added on to or formulated with the feed compositions can be as described in Section I above. In other aspects, the pheromone composition may be administered topically to the suid using an aerosol, pump spray, foam, collar, wipe, dip, liquid, gel, lotion, and/or cream. In yet other aspects, the pheromone composition may be administered by placing the composition in the environment of the suid by providing a liquid diffuser in the environment of the suid. In some aspects, the pheromone composition is administered simultaneously by adding or formulating the composition with a feed composition and by applying the composition to a surface in the pig's environment.

III. Methods of Using

One aspect of the present disclosure encompasses methods of using a pheromone composition to reduce aggressive behavior and improve feeding behavior of a suid. In some aspects, the methods comprise improving reproductive and litter performance and yield of suids. The methods comprise administering an effective amount of the pheromone composition to a suid. The methods improve performance of the suids by stimulating weight gain and final weight at market, improve feeding behavior, increase average daily gain, increase playing behavior, and combinations thereof. The pheromone composition may be as described in Section I above. Administering a composition comprising a combination of pheromonal agents may be as described in Section II above.

In some aspects, the suid is a nursing piglet. In other aspects, the suid is a weaned piglet. The composition can be administered to the animal at any time during rearing of the animal. In some aspects, the method comprises administering the pheromone composition to suids until aggressive behavior is reduced, and continuing administration of the composition after aggressive behavior is reduced. In some aspects, the composition is administered to the suid from birth until weaning. In other aspects, the composition is administered to the suid for 24 to 48 hours after weaning. In yet other aspects, the composition can be administered to the suid throughout lactation and for 24 to 48 hours after weaning.

The method of administration of the composition can be by inhalation and/or gustatory administration. In some aspects, the composition is administered by adding the agents to a feed composition.

In other aspects, the pheromonal composition is applied to a feeder in the environment of the suid. When the pheromonal composition is a pheromonal solution comprising about 5-15 mg of skatole and 7-11 mg of myristic acid, about 1 to about 50 ml, about 1 to about 30 ml, about 5 to about 25 ml, or about 20 to about 20 ml of the solution can be applied to the environment of the suid. In some aspects about 1 to about 50 mg, about 1 to about 20 mg, about 2 to about 15 mg, about 3 to about 7.5, or about 4 to about 5 mg of skatole and about 1 to about 50 mg, about 1 to about 20 mg, about 5 to about 15 mg, or about 7 to about 11 mg of myristic acid is applied to the environment of the suid.

The term "effective amount" describes an amount of pheromonal agent present in a composition sufficient to produce a noticeable effect, for example the substantial reduction in aggressive behavior upon administration to the subject, as determined according to behavioral observations described herein. The term "effective period of time" describes a period of time during which an animal is exposed to the pheromonal composition sufficient to produce a noticeable effect as described. An effective period of time may be until administration of the pheromonal agents produces a noticeable effect, or may also extend beyond the period of time required to produce the noticeable effects. As it will be recognized by individuals of skill in the art, the effective amount and duration will depend on factors such as individual animal parameters including age, physical condition, size, and weight; concurrent treatments; the frequency of treatment; the composition of the pheromonal agent; or the mode of administration. These factors are well known to those of ordinary skill in the art.

Definitions

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them unless specified otherwise.

When introducing elements of the present disclosure or the preferred aspects(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above-described cells and methods without departing from the scope of the invention, it is intended that all matter contained in the above description and in the examples given below, shall be interpreted as illustrative and not in a limiting sense.

The term "comprising" means "including, but not necessarily limited to;" it specifically indicates open-ended inclusion or membership in a so-described combination, group, series and the like. The terms "comprising" and "including" as used herein are inclusive and/or open-ended and do not exclude additional, unrecited elements or method processes. The term "consisting essentially of" is more limiting than "comprising" but not as restrictive as "consisting of." Specifically, the term "consisting essentially of" limits membership to the specified materials or steps and those that do not materially affect the essential characteristics of the claimed invention.

The terms "suid," "swine," and "pig" refer to any member of the family Suidae, hoofed mammals, order Artiodactyla, including the wild and domestic pigs, babirusas, boars, bush pigs, swine, and warthogs. Suids are stout animals with small eyes and coarse, sometimes sparse, hair. All have muzzles ending in a rounded cartilage disk used to dig for food. Some species have tusks. Suids are omnivorous and usually gregarious.

EXAMPLES

While the present invention is disclosed in reference to the preferred embodiments or examples above, it is to be understood that these embodiments or examples are intended for illustrative purposes, which shall not be treated as limitations to the present invention. It is contemplated that modifications and combinations will readily occur to those skilled in the art, which modifications and combinations will be within the spirit of the invention and the scope of the following claims.

Example 1

Depriving Piglets of Maternal Feces for the First Seven Days Post-Partum Changes Piglet Physiology and Performance before and after Weaning Coprophagy is the behavior of eating feces. This behavior has been reported in insects, rodents, lagomorphs, and other mammals including horses, swine, and some non-human primates. Coprophagy may provide an additional source of bioavailable energy and other nutrients and minerals such as protein, volatiles and non-volatile fatty acids, Zn, Cu, and Fe, especially to newborn animals. Coprophagy is also a natural mechanism by which animals establish the intestinal microbiota essential to intestinal development and the process of digestion. For instance, foals obtain vitamins, enzymes, and nutrients to compensate for nutritional deficiencies and essential bacteria for cellulose digestion via coprophagy. Similarly, coprophagy benefits rat pups since it results in the consumption of bile acids that aid the myelination process and help guard the gut against pathogenic bacteria. Furthermore, rat pup mortality due to enteritis increased when access to maternal feces was restricted. It has been estimated that nursing piglets on average eat 20 g/d of maternal feces. Different studies speculated that piglets (especially those kept outdoors) avoid anemia by obtaining iron from dirt and by eating maternal feces. Nonetheless, these studies lack an experimental group deprived of maternal feces. Furthermore, the effects of coprophagy on piglet behavior, hematology, and growth performance have not been evaluated to date. Therefore, the aim of this preliminary study was to evaluate the effect of coprophagy on these parameters by depriving piglets of maternal feces. Based on the information discussed above, the inventors hypothesized that piglets deprived of maternal feces would become anemic and will have a lower growth rate compared to the ones that had access to maternal feces.

Materials and Methods

General.

Eight litters from PIC Camborough (Pig Improvement Company, Hendersonville, TN) sows (third parity) were randomly assigned to one of two treatments (n=4) following a completely randomized design (CRD). Litters were housed in conventional slatted floor farrowing crates (1.52 m×2.13 m). Sows were fed 6.8 kg/d of a lactation corn-soybean meal (SBM) based diet (Table 1) from two weeks before the expected farrowing day until weaning. No creep feed was given to piglets during the experiment.

TABLE 1

Nutrient content and composition of sow diet.

| Diet Composition (as Fed) | |
|---|---|
| Corn, % | 56.80 |
| SBM, % | 30.00 |
| Vitamin pre-mix, % | 3.00 |
| Molasse, % | 3.65 |
| Tallow, % | 2.00 |
| Salt, % | 0.35 |

TABLE 1-continued

Nutrient content and composition of sow diet.

| | |
|---|---|
| Calcium carbonate, % | 0.70 |
| Dicalcium phosphate, % | 2.50 |
| Potassium chloride, % | 0.50 |
| Pellet binder, % | 0.50 |

Analyzed Composition * (DM basis)

| | |
|---|---|
| DM, % | 83.40 |
| CP, % | 22.00 |
| ADF, % | 4.50 |
| NDF, % | 8.00 |
| Fat, % | 5.06 |
| Ashe, % | 7.59 |
| Ca, % | 1.29 |
| P, % | 1.07 |
| Mg, % | 0.24 |
| K, % | 1.44 |
| Na, % | 0.17 |
| Fe, ppm | 650 |
| Zn, ppm | 189 |
| Cu, ppm | 24.0 |
| Mn, ppm | 144 |
| Mo, ppm | 4.00 |

DM: dry matter;
CP: crude protein;
ADF: Acid detergent fiber;
NDF: Neutral detergent fiber;
* Feed sample analyzed by Dairy One, Inc. laboratory.

Treatment and Nutritional Analysis

Figure 1B:
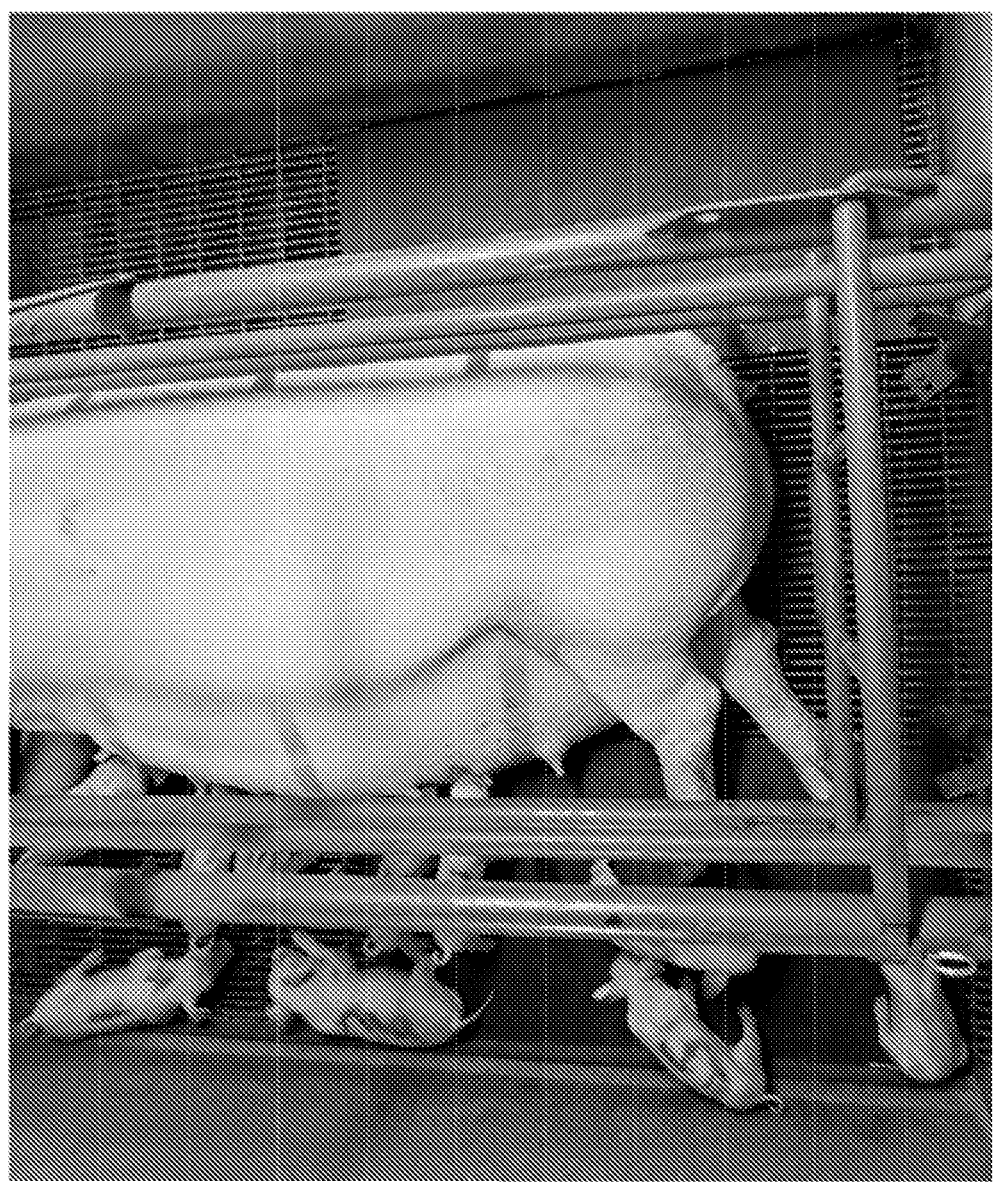
FIG. 1B depicts a photograph showing deprived litters without maternal feces.

Control (CON) litters (n=4) had free access to maternal feces, and experimental group litters (deprived group; n=4) were deprived (DEP) of maternal feces from birth until 7 d of age. Faecal deprivation was until 7 d of age since piglets will show signs of anemia at this point in time if no extraneous iron had been provided. Ten days before the expected farrowing day, sows were moved to individual farrowing crates. Until farrowing, all crates were washed daily with water to remove maternal feces. From farrowing until 7 d of age, an observer was on the farm 24 h/d weighing maternal feces immediately after defecation to determine sow faecal output and removing maternal feces from the pens of DEP litters. After being weighed by the observer, maternal feces of CON litters were placed over a rubber pad in a corner of the pen to prevent sows from blocking piglet access to feces, as well as to prevent feces from falling into the pit (FIG. 1). Faecal samples (5 g) from all sows were collected once a day (at 6 a.m.) and pooled for the duration of the study, oven dried at 55° C. for 48 h, and used for determination of the nutrient contents. Dietary and faecal sample nutrient analyses were performed at the Dairy One, Inc. laboratory (Ithaca, NY). Faecal true protein (TP) concentration was measured using the bicinchoninic acid (BCA) assay kit (Thermo Fisher Scientific, Bellefonte, PA) according to the manufacturer's instructions. After 7 d of age, piglets in both treatment groups had free access to maternal feces. Piglets were ear notched, teeth clipped, injected with iron dextran and penicillin, and then castrated (males only) at 7 d of age.

Pre-Weaning Performance, Blood Collection and Behavior

Pre-weaning survival and mortality rates, body weight (BW), and average daily gain (ADG) of piglets were evaluated at 0, 7, and 21 d of age. Blood samples (~1 mL) were collected into $K_2$ EDTA vacutainer tubes from one male and female piglet from each litter via jugular venipuncture at 0, 7, and 21 d of age. Piglets were selected at random from those with body weights close to the average body weight of the litter. An automated cell counter (Vet Scan HM 5; Abaxis) was used to evaluate hemoglobin (Hb), hematocrit (HCT), mean corpuscular volume (MCV), red blood cells (RBC), and white blood cells (WBC). The neutrophil to lymphocytes (NLR) ratio was calculated for the data obtained. Hematological values from both piglets within a litter were averaged. The average value was considered to be a representative value of the litter and used for the statistical analysis.

Piglet behaviors including nursing, laying, fighting, and active behaviors were evaluated for 24 h on the 7th day of age, the last day of faecal deprivation. In addition, the time at least one piglet from the litter was observed interacting with maternal feces was recorded for control litters. For this, video cameras were placed over the farrowing crates to record the behavior of the entire litter. Definitions of behavioral observations are given in Table 2. To evaluate high frequency behaviors (laying, active, standing) a trained observer conducted a ten-minute scan sample for 24 h. A continuous sampling technique was used to quantify low frequency behaviors such as interaction with feces, fighting and nursing behaviors. For each litter, the duration of a nursing bout, bout interval, and the number of bouts per hour were recorded. All behavioral data were observed by a single observer and no observation software was used to code behavioral data.

TABLE 2

Behavior definitions

| Behavior | Definition |
|---|---|
| Laying | Lying on one side, four legs, or sternum |
| Standing | Straight up on four legs without moving any leg |
| Active | Walking or running through the pen. Sniffing, touching, or rubbing other piglets or pen walls or floor |
| Fighting | Biting or pushing another piglet |
| Nursing | From the moment 90% of the litter stop massaging the udder, remain still and began suckling until the time 10% of the litter start massaging the udder again or stop suckling. |
| Interacting with maternal feces | The amount of time piglets within a litter spent rooting, sniffing, touching, eating, or playing with maternal feces |

Post-Weaning Performance

Piglets were weaned at 25±2 d of age. To keep the experimental unit intact, at the time of weaning, the piglets from each litter were kept together and moved to nursery pens. Raised pens measuring 1.5×3 m, with slat plastic floor were used as nursery pens. Piglets in both treatments were housed in the same barn. After weaning, average daily feed intake (ADFI), ADG, and feed-to-gain ratio (F:G) were measured weekly for a period of four weeks. ADFI was calculated by estimating weekly feed consumption by weighing the remaining feed on the feeder. ADG was calculated by weekly changes in piglets body weight. F:G was the ratio between ADFI and ADG. Four weeks after weaning, litters were moved to the farm growing-finishing facility as described above. Finishing pens were each 3.65× 2.15 m with a slat concrete floor. Measures of growth performance (ADG, ADFI, and F:G) were evaluated monthly until 123 d post weaning. During the post-weaning period, pigs were fed corn-SBM based diets according to the phase-feeding program.

Statistical Analysis

Data were analyzed as a CRD in SAS (SAS version 9.4; SAS Inst., Inc., Cary, NC, USA). Litter was considered the experimental unit (N=8). Normality and homogeneity of variances were confirmed using the univariate procedure (PROC UNIVARIATE). A repeated measure analysis of variance (PROC GLIMMIX) was used to evaluate parameters measured over time, such as blood cell counts and performance data. The model included the effect of time, treatment, and their interaction as fixed effects and litter within treatment (experimental unit) as a random effect. Litter size (LS) was used as co-variate. A first order auto regressive co-variance structure was included in the model since it produced the smallest AIC value. Fisher's least significant difference (LSD) was used to determine any treatment effect within the period. A one-way ANOVA was used to evaluate litter behavior at 7 d of age. The effect of days post-partum on sow faecal output was evaluated using the Friedman test since data did not meet parametric assumptions. To simplify our discussion, the presented means and standard errors (SE) correspond to the raw data and not to the ranks. Differences were considered significant when $p \leq 0.05$.

Results

Sow Fecal Output and Nutrient Content

Figure 2:
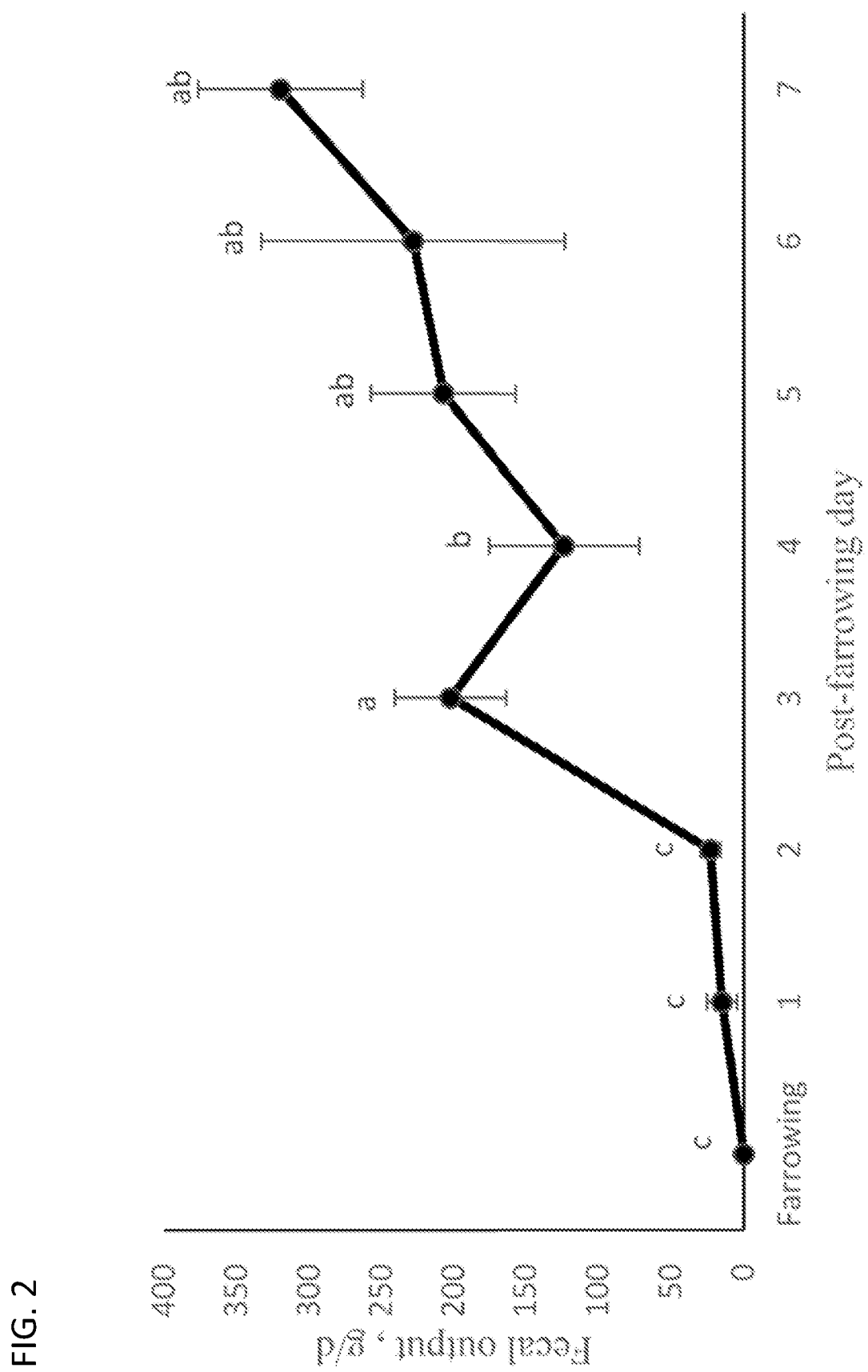
FIG. 2 depicts a graph showing fecal output (DM basis) ±standard errors (SE) of sows (n=8) after farrowing. The data presented are Least squares means±SE and represent the best estimate of means that was obtained using repeated measurements. Days with different superscripts are significantly different from each other based on Friedman test ($p<0.05$).

The nutrient contents of sow faecal samples are presented in Table 3. Faecal output was not affected by treatment. Sow faecal output (DM basis) was significantly affected by post-partum day ($T_{7,55}=-2.72$; $p<0.01$). None of the sows defecated on the day of farrowing and only two and three sows defecated on day one and two post-farrowing, respectively. All sows defecated daily after 3 d post-partum. Faecal output was significantly lower at farrowing and at days one and two post-partum relative to the other days ($p<0.01$). Fecal output the third day post-partum did not differ from 5, 6, and 7, but was higher than day four fecal output (FIG. 2). On average, sows defecate 216±24.8 g of DM daily from day 3 to 7 post-partum.

TABLE 3

Analyzed nutrient contents (DM basis) of lactating sow feces.

| Analyzed Composition * | (n = 8) | SE |
|---|---|---|
| DM, % | 37.5 | 0.55 |
| CP, % | 21.1 | 0.43 |
| TP, % | 16.3 | 0.98 |
| ADF, % | 7.95 | 0.62 |
| NDF, % | 21.4 | 1.41 |
| Fat, % | 3.99 | 0.30 |
| Ashes, % | 31.7 | 0.60 |
| Ca, % | 6.36 | 0.17 |
| P, % | 4.76 | 0.15 |
| Mg, % | 1.46 | 0.04 |
| K, % | 0.64 | 0.06 |
| Na, % | 0.14 | 0.02 |
| Fe, ppm | 4039 | 137 |
| Zn, ppm | 1257 | 40.2 |
| Cu, ppm | 244 | 11.8 |
| Mn, ppm | 990 | 29.2 |
| Mo, ppm | 5.17 | 0.26 |

* Mean value of each nutrient; SE: standard error of the means; DM: dry matter; CP: crude protein; TP: True protein; ADF: Acid detergent fiber; NDF: Neutral detergent fiber.

Measures of Behavior

Data from one litter in the CON group was excluded from analysis due to problems with the recording system. No treatment effects were observed on measures of litter nursing, laying, active, standing, or fighting behaviors at 7 d of age (Table 4). Behavioral data showed that at 7 d of age, piglets within a litter spent 4.27±0.51 min interacting with maternal feces per day.

TABLE 4

Control (CON) and deprived (DEP) litter behaviors at 7 d of age.

| | Treatments | | | |
|---|---|---|---|---|
| Behavior | CON (n = 3) | DEP (n = 4) | SE | p-Value |
| Nursing duration, s | 66.7 | 62.3 | 4.46 | 0.49 |
| Nursing interval, m | 42.6 | 42.4 | 3.11 | 0.95 |
| Nursing per hour | 1.38 | 1.40 | 0.12 | 0.89 |
| Laying, % | 73.1 | 72.2 | 2.00 | 0.70 |
| Active, % | 7.00 | 5.00 | 1.00 | 0.22 |
| Standing, % | 5.60 | 5.20 | 1.20 | 0.82 |
| Fighting, m/d | 5.41 | 6.08 | 3.42 | 0.89 |
| Feces interaction, m/d | 4.27 | — | 0.51 | — |

Piglet Hematology and Survival

Table 5 shows CON and DEP litters pre-weaning hematology and mortality and survival rates. Litter size (LS) was not affected by treatment. A co-variate effect on mortality rate, survival rate, WBC, and neutrophil (NEU) counts, as well as the neutrophil lymphocyte ratio (NLR) was observed ($p<0.05$). There was a significant treatment effect for WBC counts ($F_{1,6}=16.05$; $p<0.01$). The WBC count was higher in CON pigs than in DEP pigs during the first 21 d of age. A time effect ($p<0.05$), was found for all blood parameters but not for litter survival rate and WBC. Red blood cells, Hb, MCV, and HCT levels were lower at 7 d of age than at birth ($p<0.05$), but at 21 d of age, RBC, Hb, and HCT values were higher than they were at birth. At 21 d of age, MCV values were similar to the MCV observed at birth. Lymphocytes (LYM) and monocytes (MON) blood counts increased at 7 d of age ($p<0.05$). No difference was observed between LYM counts at 21 and 7 d of age. Monocyte counts at 21 d of age were similar to the ones observed at birth. The interaction effects between treatment and time was significant for NLR ($F_{2,11}=27.54$; $p<0.01$). At birth, control piglets had higher NLR than DEP piglets (4.69 vs 2.15±0.21), but no differences were observed after birth.

TABLE 5

Survival rate and complete blood cell count in piglets with (CON) or without (DEP) access to maternal feces at birth, 7, and 21 d of age.

| Dependent Variables | Birth (n = 8) | | 7 d (n = 8) | | 21 d (n = 8) | | SE [1] | p•Value [2] | | | |
|---|---|---|---|---|---|---|---|---|---|---|---|
| | CON | DEP | CON | DEP | CON | DEP | | TRT | Time | Interaction | LS [3] |
| Litter Size | 15.2 [a] | 15.7 [a] | 13.2 [b] | 12.5 [b] | 13.0 [b] | 11.7 [b] | 1.25 | 0.77 | <0.01 | 0.46 | • |
| Modality rate, % | • | • | 16.0 | 19.0 | 16.1 | 19.1 | 0.83 | 0.77 | 0.61 | 0.73 | <0.01 |

TABLE 5-continued

Survival rate and complete blood cell count in piglets with (CON) or without (DEP) access to maternal feces at birth, 7, and 21 d of age.

| Dependent Variables | Birth (n = 8) | | 7 d (n = 8) | | 21 d (n = 8) | | SE [1] | p•Value [2] | | | LS [3] |
|---|---|---|---|---|---|---|---|---|---|---|---|
| | CON | DEP | CON | DEP | CON | DEP | | TRT | Time | Interaction | |
| Survival rate, % | • | • | 84.0 | 81.2 | 83.9 | 80.9 | 7.54 | 0.80 | 0.54 | 0.72 | <0.01 |
| WBC, $10^9$/L | 16.2 [d] | 9.79 [e] | 10.3 [d] | 10.1 [e] | 12.6 [d] | 9.52 [e] | 1.25 | <0.01 | 0.18 | 0.12 | 0.05 |
| Lymphocyte, $10^9$/L | 2.89 [b] | 3.03 [b] | 6.32 [a] | 5.79 [a] | 8.09 [a] | 6.06 [a] | 0.70 | 0.217 | <0.01 | 0.26 | 0.48 |
| Monocyte, $10^9$/L | 0.115 [b] | 0.130 [b] | 0.766 [a] | 0.775 [a] | 0.212 [b] | 0.456 [b] | 0.14 | 0.44 | <0.01 | 0.63 | 0.66 |
| Neutrophl, $10^9$/L | 13.16 [u] | 6.60 [v] | 3.21 [w] | 3.54 [vw] | 4.34 [vw] | 3.07 [w] | 1.07 | <0.01 | <0.01 | 0.01 | 0.02 |
| NLR | 4.69 [u] | 2.15 [v] | 0.534 [w] | 0.637 [w] | 0.543 [w] | 0.490 [w] | 0.21 | <0.01 | <0.01 | <0.01 | 0.05 |
| RBC, $10^9$/L | 6.24 [b] | 5.51 [b] | 4.95 [c] | 5.05 [c] | 6.99 [a] | 6.98 [a] | 0.37 | 0.61 | <0.01 | 0.16 | 0.22 |
| Hemoglobin, g/dL | 10.70 [b] | 10.42 [b] | 7.42 [c] | 8.48 [c] | 12.54 [a] | 12.66 [a] | 0.56 | 0.63 | <0.01 | 0.14 | 0.25 |
| Hematocrit, % | 35.48 [b] | 34.40 [b] | 22.93 [c] | 26.22 [c] | 40.15 [a] | 40.55 [a] | 1.95 | 0.67 | <0.01 | 0.22 | 0.21 |
| Mean corpuscular volume, fl | 57.42 [a] | 62.45 [a] | 45.94 [b] | 51.68 [b] | 57.52 [a] | 57.92 [a] | 2.00 | 0.07 | <0.01 | 0.27 | 0.65 |
| Mean corpuscular hemoglobin, pg | 17.3 [a] | 19.0 [a] | 15.0 [b] | 16.8 [b] | 18.0 [a] | 18.1 [a] | 0.69 | 0.138 | <0.01 | 0.18 | 0.53 |

[a, b, c] Means with different subscripts differ due to time effect (p•values < 0.05);
[d, e] Means with different subscripts differ due to treatment effect within time (p•values < 0.05);
[u, v, w] Means with different subscripts differ due to time × treatment interaction (p•values < 0.05);
[1] Largest SE of least squares means;
[2] Significant level for main effect of treatment, time, and treatment × time interaction;
[3] Significant level of LS as a covariate.

Pre and Post-Weaning Growth Performance

Piglet pre- and post-weaning growth performance data are presented in Table 6. The main effect of treatment was significant for piglet ADG ($F_{1,6}$=20.48; p<0.01) and post-weaning ADFI ($F_{1,6}$=8.52; p=0.02). Piglets in the control group were significantly heavier than DEP piglets after 56 d post-weaning. At 123 d post-weaning, control piglets were 9.3 kg heavier than treatment pigs (100.7 vs 91.4±2.29 kg; p<0.01). Overall, there was no treatment effect on the F:G ratio, but control litters had a greater ADG (0.536 vs 0.483±0.008) and ADFI (0.998 vs 0.901±0.023) than DEP piglets.

TABLE 6

Pre and post-weaning performance of piglets with (CON) and without (DEP) access to maternal feces.

| Item Body Weight, kg | CON (n = 4) | DEP (n = 4) | SE | p-Value [1] |
|---|---|---|---|---|
| Birth | 1.45 | 1.30 | 0.150 | 0.94 |
| 7 d of age | 2.72 | 2.37 | 0.141 | 0.845 |
| 21 d of age | 6.45 | 6.07 | 0.146 | 0.83 |
| Weaning | 7.75 | 7.43 | 0.140 | 0.85 |
| 7 d post-weaning | 9.21 | 8.54 | 0.175 | 0.71 |
| 14 d post-weaning | 11.8 | 10.9 | 0.287 | 0.65 |
| 21 d post-weaning | 15.53 | 13.98 | 0.442 | 0.40 |
| 28 d post-weaning | 18.7 | 17.2 | 0.543 | 0.42 |
| 56 d post-weaning | 33.5 | 29.9 | 1.23 | 0.058 |
| 73 d post-weaning | 48.8 [a] | 43.4 [b] | 1.65 | <0.01 |
| 102 d post-weaning | 75.0 [a] | 66.7 [b] | 1.89 | <0.01 |
| 123 d post-weaning | 100.7 [a] | 91.4 [b] | 2.29 | <0.01 |
| ADG, kg/d | | | | |
| 7 d of age | 0.18 | 0.15 | 0.014 | 0.49 |
| 21 d of age | 0.27 | 0.26 | 0.014 | 0.86 |
| Weaning | 0.30 | 0.30 | 0.014 | 0.99 |
| 7 d post-weaning | 0.21 | 0.16 | 0.019 | 0.25 |
| 14 d post-weaning | 0.37 | 0.35 | 0.022 | 0.55 |
| 21 d post-weaning | 0.54 [a] | 0.43 [b] | 0.027 | 0.020 |
| 28 d post-weaning | 0.45 | 0.45 | 0.028 | 0.87 |
| 56 d post-weaning | 0.52 | 0.44 | 0.028 | 0.10 |
| 73 d post-weaning | 0.89 | 0.81 | 0.033 | 0.12 |
| 102 d post-weaning | 0.90 [a] | 0.76 [b] | 0.041 | <0.01 |
| 123 d post-weaning | 1.23 | 1.16 | 0.062 | 0.15 |
| ADFI, kg/d | | | | |
| 7 d post-weaning | 0.27 | 0.23 | 0.016 | 0.15 |
| 14 d post-weaning | 0.45 | 0.43 | 0.017 | 0.73 |
| 21 d post-weaning | 0.76 | 0.70 | 0.045 | 0.32 |
| 28 d post-weaning | 0.84 | 0.78 | 0.047 | 0.34 |
| 56 d post-weaning | 1.41 | 1.29 | 0.038 | 0.058 |
| 73 d post-weaning | 2.25 [a] | 2.01 [b] | 0.059 | <0.01 |
| F:G | | | | |
| 7 d post-weaning | 1.33 | 1.48 | 0.091 | 0.31 |
| 14 d post-weaning | 1.22 | 1.25 | 0.041 | 0.86 |
| 21 d post-weaning | 1.41 | 1.64 | 0.060 | 0.13 |
| 28 d post-weaning | 1.87 | 1.76 | 0.141 | 0.44 |
| 56 d post-weaning | 2.69 | 2.87 | 0.119 | 0.20 |
| 73 d post-weaning | 2.52 | 2.46 | 0.099 | 0.62 |
| Overall performance | | | | |
| *ADG (kg/day) | 0.54 [a] | 0.48 [b] | 0.008 | <0.01 |
| +ADFI (kg/day) | 0.99 [a] | 0.90 [b] | 0.023 | 0.02 |
| +F:G | 1.84 | 1.91 | 0.071 | 0.36 |

SE = Largest SE of least squares means;
[a, b] Within a row, least squares means without a common superscript differ (p < 0.05) due to treatment effect;
*Overall ADG from birth until 123 d post-weaning;
+Overall ADFI and F:G ratio from weaning until 73 d post-weaning.

Discussion

The aim of the study was to evaluate the effects of coprophagy on piglet blood cell counts, behavior, and performance. Coprophagy benefits were studied by depriving piglets of maternal feces until 7 d of age. From days 3 to 7 post-partum, sows excreted close to one kilogram of wet feces or around 216±24.80 g of DM per day. The low or absent faecal output observed during the first two days post-partum can be associated with the reduction in feed intake that often occurs around the time of farrowing in modern pig production units since low feed intake reduces the passage rate of digesta. Based on the estimated faecal output and assuming an average litter size of 10 pigs, each pig could eat 21.62 g of feces per day. This is in general agreement with estimation of piglet faecal consumption known in the art.

Piglets were deprived of maternal feces for only 7 d since at this time point piglets should be presenting signs of anemia if no external iron is provided due to their rapid growth rate, rapid increase in blood volume, and the low iron content of sow milk. This allowed us to study the effect of faecal deprivation without affecting the piglets' welfare. After deprivation of maternal feces, no treatment effects were found on piglet RBC, Hb, HCT, MCV, or any other blood parameters associated with the diagnosis of anemia at 0, 7, or 21 d of age. At 7 d of age, piglets in both treatment groups had RBC, MCV, HCT, and Hb, levels like the ones found in mildly anemic piglets. In addition, behavior data showed that both groups lying behavior was higher than the ones reported in 5 d old piglets, which could be another sign of mild anemia. After day 7, erythrocyte parameters improved since all piglets received 2 mL of iron dextran. Thus, contrary to what has been reported in the past, coprophagy did not prevent anemia in this study. It is possible that to see any effects on RBC parameters, longer periods of deprivation are required. However, hemoglobin differences in this study did not indicate any trends, so it is unlikely that piglet faecal intake can greatly impact red blood cell or hemoglobin levels in a commercial setting.

Control litters had higher WBC counts at birth and until 21 d of age. Differences in WBC, NEU, and NLR observed at birth can be a consequence of differences in bleeding time. Due to limitations with birth times, blood samples were taken in different time points, which led to variability in piglet colostrum intake. Since three out of the four litters in the control group were bled overnight, control piglets could have higher WBC count since they had more time to consume colostrum [19]; however, we think this is unlikely. Nevertheless, control litters WBC continued to be higher until 21 d of age. This was expected since control piglets were exposed to feces for more time. By eating or being in contact with maternal feces, piglets may have internalized the maternal faecal microbiota. The latter can lead to the development of an acquired immune system and the proliferation of WBC. These results showed that having access to maternal feces early in life might improve piglet immunocompetence.

In the current study, although having access to maternal feces did not improve piglet red blood cell parameters associated with anemia, it improved piglet growth performance. At 123 d post-weaning, control litters remained heavier and had a higher ADG and ADFI. Piglets iron intake can impact growth rate. Piglets need to consume 7 mg of iron per day or 21 mg of iron per kilogram of body weight gained. Because of this, heavier piglets tend to have lower values of RBC, Hb, HCT. The greater blood volume and iron requirement of fast-growing pigs makes them prone to iron deficiency anemia. Thus, deprivation of maternal feces could have limited piglet iron ingestion leading to lower growth rate in the DEP group. We are still elucidating the possible mechanisms by which having access to maternal feces early in life improved piglet growth performance.

Based on our findings, it is speculated that early exposure to maternal feces improved piglet growth performance through a nutritional and/or microbiological effect. In addition, the presence of maternal semiochemicals in lactating sow feces could also play a significant role in these findings. Most likely the benefits of early exposure to maternal feces on piglet growth performance is due to an interaction between these possible mechanisms.

As faecal nutrient content analyses showed, lactating sow feces are rich in minerals (Fe, Zn, Cu, and Mn) and have a high concentration of true protein. By eating maternal feces, piglets may obtain bioavailable nutrients that promote their growth and promote gut health. For instance, feces are rich in Cu and Zn, minerals that have antibacterial and growth stimulating properties. It has been shown that supplementing 250 ppm of Cu and/or Zn in weaning diets increases post-weaning performance. Hence, we speculate that coprophagy might increase piglet mineral and nutrient intake, therefore enhancing performance and guarding the piglet gut against pathogenic bacteria.

Another possibility is that maternal feces provided piglets with essential bacteria that are beneficial to the gastrointestinal tract, as in other species. Since current housing conditions allow pigs to be in contact with sow skin, vulva, feces, and urine, piglet microbiome is likely to be dependent on the sow. Microbial transfer from sow to piglets starts when piglets exit the birth canal and continues via colostrum, milk, and feces consumption. Furthermore, during piglets first week, piglet and sow faecal metabolic fingerprints are alike. Thus, faecal deprivation during the first week of age could have prevented early colonization of beneficial bacteria from sow feces. Studies in humans suggest that disruption in the early colonization of the gastrointestinal tract can have long-term health consequences. In piglets, the development of the mucosal immune system is dependent on piglet microbial exposure. Thus, we hypothesized that coprophagy may allow piglets to obtain beneficial microbes from maternal feces. These microbes may help piglets maintain a proper intestinal environment and develop the mucosal immune system thereby enhancing their performance. This might also explain why CON piglets had higher WBC counts. Future studies of healthy lactating sow faecal microbiome may result in the discovery of beneficial bacterial populations that could be used as a species-specific probiotic.

Lastly, deprivation of maternal feces could reduce piglet growth performance by removing maternal semiochemicals from the environment. Faecal maternal semiochemicals have been reported in other species that also exbibit coprophagy behavior. For instance, rat dams secrete a maternal faecal pheromone (deoxycholic acid) which attracts pups and promotes coprophagy. Similar to rats, previous studies have found that piglets have a preference for maternal feces compared to other maternal odors as early as 12 h of life. As in rat pups, this preference may be caused by maternal semiochemicals present in lactating sow feces. Maternal semiochemicals have been shown to improve weaning piglet performance. For instance, the pig appeasing pheromone and the rabbit maternal pheromone (2-methyl-2-butenal) reduced aggression and improved performance when sprayed on the feeders of weaned piglets [30,31]. Thus, it is possible that sow feces contain natural maternal semiochemicals that promote health and performance. Future studies are needed to identify maternal semiochemicals in lactating sows that could enhance piglet growth performance.

Conclusions

In this preliminary study, the effects of faecal deprivation on piglet hematology, behavior, and growth were evaluated by depriving piglets of maternal feces for the first 7 d of life. Depriving piglets of maternal feces had no significant effect on piglet behavior. Deprivation of maternal feces reduced the piglets' WBC counts. By having access to maternal feces early in life, piglets improved their pre-and post-weaning performance. Data suggest that early exposure to maternal feces improves piglet performance and immunocompetence. It is speculated that the presence of faecal maternal semiochemicals might induce coprophagy, and that by consuming maternal feces piglets may obtain nutrients and beneficial microbes that have long-term effects on their performance.

Example 2

Identification of Faecal Maternal Semiochemicals in Swine (Sus scrofa) and their Effects on Weaned Piglets Several behavioral studies have demonstrated that piglets are attracted to their mothers' faeces as early as 12 hours after birth and can even discriminate between maternal and non-maternal faeces. Moreover, it has been shown that piglets are attracted to lactating sow faeces when tested against non-lactating sow faeces. This suggests that during lactation, sows might be secreting maternal faecal semiochemicals that attract piglets. At first glance, the biological benefits of swine faecal semiochemicals may seem unobvious. Notwithstanding, maternal faecal pheromones have been reported in other animals. For instance, like piglets, rat pups are attracted to maternal faeces and both species consume maternal faeces. Rat dams secrete a maternal faecal pheromone (deoxycholic acid) from the $14^{th}$ to the $27^{th}$ day of lactation that attracts pups and promotes coprophagy. By eating maternal faeces, rat pups obtain bile acids that aid the myelination process and guard the guts against pathogenic bacteria.

Although not fully studied, scientists believed that coprophagy helps piglets to prevent anaemia. In a previous study, The inventors found that piglets deprived of maternal faeces for their first seven days of age had lower growth rate than those exposed to maternal faeces early in life. In this study, it is speculated that, as in rats, maternal semiochemicals might be attracting piglets and inducing coprophagy. However, to date, changes in the nutritional value of lactating sow faeces and in its volatile profile has not been evaluated. Since rat pups and piglets exhibit coprophagy behavior and this behavior is beneficial to both species, we hypothesize that, as in rats, maternal semiochemicals could be responsible for piglet preference towards maternal faeces and of inducing coprophagy. Hence, the objectives of this study were: (1) The identification of swine maternal faecal semiochemi-cals that could be attracting piglets. (2) Evaluate changes in lactating sow faeces nutrient content. (3) Evaluate piglets preference for faecal maternal semiochemicals and their effects on piglet behavior and performance when sprayed on the weaning environment. For this, the nutrient content and volatile profile of gestating and lactating sow faeces were compared and tests with possible candidate semiochemicals were conducted.

Results

Faeces Nutritional Value.

Even when sows were given the same amount of feed, gestating sows had higher feed intake than lactating sows. Faecal dry matter, acid detergent fiber, ashes, true protein (TP), Ca, Mg, K, Zn, Cu, and Mn changed with sow reproductive state. During lactation, faecal dry matter, ash, TP, Mg, Zn, and Cu increased whereas the acid detergent fiber, Ca, and K decreased (Table 1). No differences in faecal crude protein (CP), neutral detergent fiber, fat, P, Na, Fe, Mn, and Mo were observed.

Identification of Maternal Semiochemicals.

Figure 3:
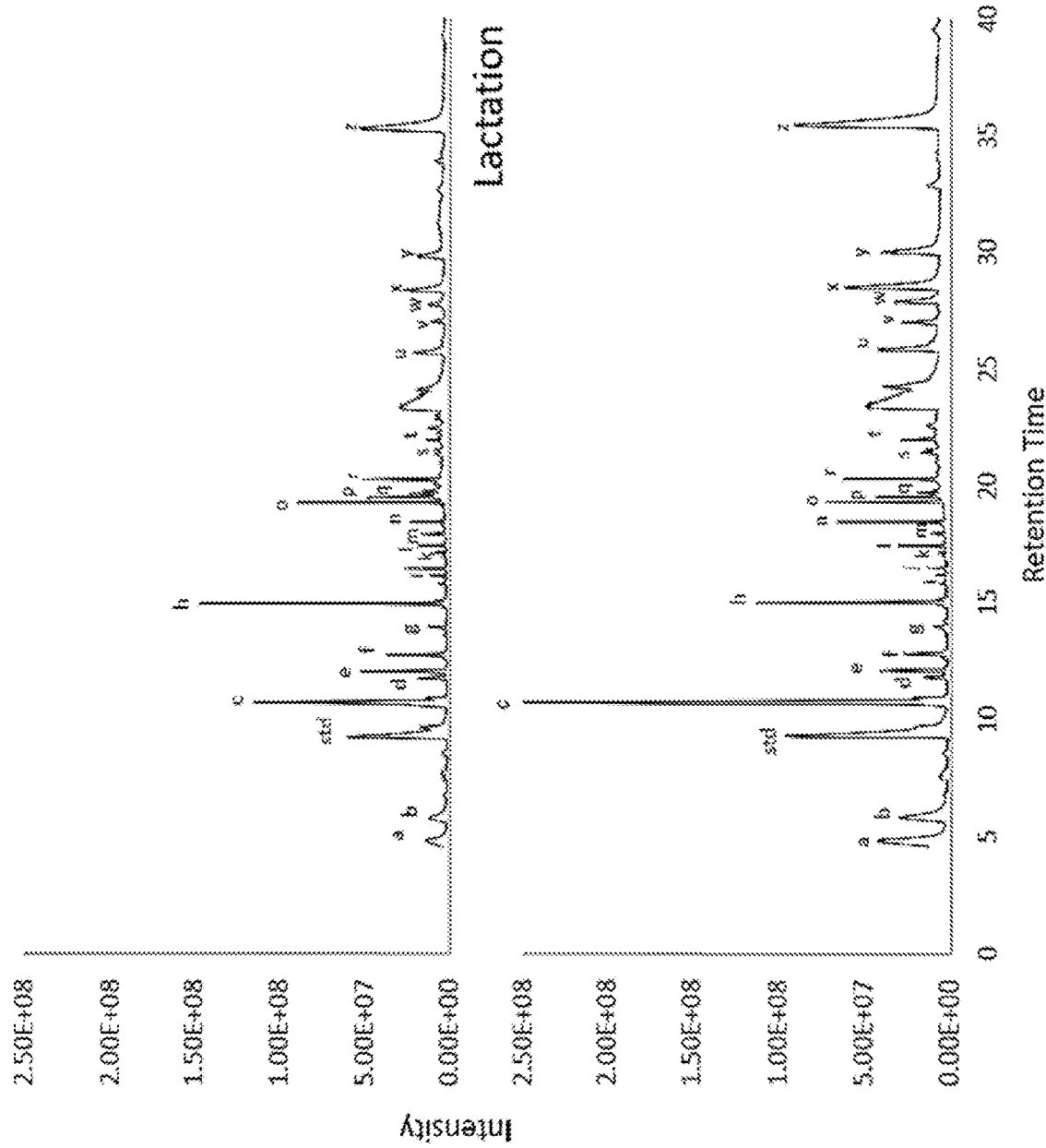
FIG. 3 depicts representative chromatogram of gestating and lactating sow faeces volatiles.

FIG. 3 shows a representative chromatogram of gestating and lactating sow faecal extract. The present study identified 26 volatile organic compounds (VOCs) in sow faeces during gestation and lactation (Table 7). Of these, 15 were confirmed using analytical standards mass spectrum and retention time. The number of volatiles present in faeces was not different during lactation or gestation. Neither gestating nor lactating sow faecal matter had unique volatiles. Nevertheless, the peak area ratio of seven volatiles (Table 8) significantly changed after farrowing. At the beginning of lactation, the peak area ratio of skatole (P=<0.01), myristic acid (P=0.01), and two unknown molecules (P=0.02 and P=0.01) increased whereas the area ratio of methyl (Z)-octadec-9-enoate (P=0.001), 13-octadecanoic acid-methyl ester (P=0.03), and methyl octadeca-9,12-dienoate (P=0.01) significantly decreased. Using calibration curves and correcting for faecal dry matter differences between periods, the faecal concentration of candidate semiochemicals whose peak area ratio significantly changed were estimated. Table 9 shows the 95% confidence interval of the estimated concentration of these analytes in wet faeces and on dry matter basis. On wet faeces, skatole and myristic acid faecal concentration significantly increased whereas methyl octadeca-9,12-dienoate concentration significantly decreased during lactation. However, after correcting for faecal dry matter differences between periods, only skatole and methyl octadeca-9,12-dienoate concentrations were significantly different between periods (P<0.05).

TABLE 7

| | Period | | | |
|---|---|---|---|---|
| Nutrient | Gestation (N = 8) | Lactation (N = 8) | SE[a] | P value[b] |
| FI, kg/d | 5.28 | 3.71 | 0.34 | 0.01 |
| DM, % | 33.35 | 37.51 | 0.55 | <0.01 |
| CP, % | 21.86 | 21.10 | 0.43 | 0.29 |
| TP, % | 12.64 | 16.33 | 0.98 | <0.01 |
| ADF, % | 8.81 | 7.95 | 0.62 | 0.04 |
| NDF, % | 23.54 | 21.38 | 1.41 | 0.14 |
| Fat, % | 4.20 | 3.99 | 0.30 | 0.73 |
| Ash, % | 28.63 | 31.74 | 0.60 | <0.01 |
| Ca, % | 6.84 | 6.36 | 0.17 | <0.01 |
| P, % | 4.62 | 4.76 | 0.15 | 0.21 |
| Mg, % | 1.30 | 1.46 | 0.04 | <0.01 |
| K, % | 0.82 | 0.64 | 0.06 | <0.01 |
| Na, % | 0.17 | 0.14 | 0.02 | 0.23 |
| Fe, ppm | 4237 | 4038 | 137 | 0.26 |
| Zn, ppm | 1084 | 1257 | 40.2 | <0.01 |
| Cu, ppm | 153 | 244 | 11.8 | <0.01 |
| Mn, ppm | 832 | 989 | 29.2 | <0.01 |
| Mo, ppm | 5.56 | 5.17 | 0.26 | 0.07 |

[a]Letter corresponds to peaks in FIG. 3.
RT = Retention time.
[1] Based peak of molecule mass spectrum
[2] Similarity between obtained mass spectrum and NIST library database for the candidate molecule.
* Candidate molecule confirmed with its analytical standard.
IUPAC = International union of pure and applied chemistry.

TABLE 8

Faecal volatiles peak area ratio.

| Candidate Molecule IUPAC name | Gestation (N = 8) | Lactation (N = 8) | SE[a] | P value[b] |
|---|---|---|---|---|
| 3-Methylbutanoic acid* | 0.07 | 0.09 | 0.03 | 0.57 |
| Pentanoic acid* | 0.05 | 0.05 | 0.03 | 0.99 |
| 4-Methylphenol* | 0.95 | 0.93 | 0.06 | 0.77 |
| Methyl 13-Methyltetradecanoate | 0.07 | 0.09 | 0.01 | 0.11 |
| Methyl 12-Methyltetradecanoate | 0.19 | 0.25 | 0.03 | 0.19 |
| Methyl pentadecanoate* | 0.14 | 0.15 | 0.02 | 0.58 |
| Methyl 14-Methylpentadecanoate | 0.03 | 0.04 | 0.01 | 0.42 |
| Methyl hexadecanoate* | 0.52 | 0.38 | 0.07 | 0.10 |
| Methyl 14-Methyl Hexadecanoate | 0.02 | 0.03 | 0.01 | 0.10 |
| Methyl 15-Methyl Hexadecanoate | 0.03 | 0.04 | 0.01 | 0.10 |
| Methyl heptadecanoate* | 0.01 | 0.01 | <0.01 | 0.40 |
| 1H-Indole* | 0.07 | 0.04 | 0.01 | 0.06 |
| Hexadecan-1-ol | 0.03 | 0.03 | 0.01 | 0.95 |
| 3-Methylindole (skatole)* | 0.09 | 0.23 | 0.02 | <0.01 |
| Methyl Octadecanoate* | 0.22 | 0.20 | 0.02 | 0.52 |
| Methyl (Z)-octadec-9-enoate* | 0.25 | 0.13 | 0.03 | 0.01 |
| 13-Octadecanoic acid, Methyl ester | 0.10 | 0.06 | 0.01 | 0.03 |
| Methyl octadeca-9,12-dienoate* | 0.24 | 0.15 | 0.02 | 0.01 |
| Methyl (9Z,12Z,15Z)-octadeca-9,12,15-trienoate* | 0.01 | 0.02 | <0.01 | 0.47 |
| Methyl (Z)-heptadec-10-enoate | 0.09 | 0.09 | 0.01 | 0.92 |
| Tetradecanoic acid (myristic acid)* | 0.17 | 0.24 | 0.02 | 0.01 |
| 1,3-dihydroindol-2-one | 0.07 | 0.06 | 0.01 | 0.24 |
| Unknown | 0.09 | 0.23 | 0.05 | 0.02 |
| Unknown | 0.27 | 0.43 | 0.04 | 0.01 |
| Pentadecanoic acid* | 0.15 | 0.23 | 0.04 | 0.12 |
| Hexadecanoic acid* | 0.89 | 0.91 | 0.07 | 0.841 |

[a]SE standard error of the difference.
[b]Significance level of period (Gestation or Lactation) effect.
IUPAC—International union of pure and applied chemistry.
*Candidate molecule confirmed with its analytical standard.

TABLE 9

Candidate semiochemicals estimated concentration.

| Candidate analyte | | Gestation CI* | Lactation CI* | P value |
|---|---|---|---|---|
| Skatole | [a]μg/g | 7.68-15.69 | 27.29-35.30 | <0.01 |
| | DM basis | 23.84-46.25 | 72.44-94.85 | <0.01 |
| Methyl octadeca-9,12-dienoate | [a]μg/g | 16.17-25.13 | 9.14-18.10 | 0.03 |
| | DM basis | 48.23-76.23 | 22.70-50.69 | 0.01 |
| Myristic acid | [a]μg/g | 62.52-69.96 | 71.23-78.67 | □0.01 |
| | DM basis | 186.93-210.46 | 188.58-212.11 | 0.83 |

CI*—Lower and upper 95% confident interval.
DM basis—μg/g of dry matter.
[a]Wet (fresh) faeces basis.

Preference Test.

Table 10 shows the overall preference index (PI) and the percentage of time piglets spent interacting with feeders sprayed with a solution containing skatole, myristic acid or both semiochemicals. The overall percentage of time piglets interacted with the feeders (P=0.02) and the preference index (P=0.05) showed that piglets preferred the feeder sprayed with a solution containing skatole and myristic acid when compared to a control. No preference or aversion was found when skatole and myristic acid were sprayed individually. Although piglets interacted with the feeders, no feed was consumed during the trials. Thus, feed intake assessment was not possible.

TABLE 10

Maternal semiochemicals preference assessment.

| Comparison | | Molecule | Control | SE* | N | P value |
|---|---|---|---|---|---|---|
| Both[a] vs | PI | 0.54 | 0.46 | 0.02 | 9 | 0.05 |
| Control | % | 1.02 | 0.83 | 0.11 | | 0.02 |
| Skatole vs | PI | 0.51 | 0.50 | 0.02 | 8 | 0.74 |
| Control | % | 0.54 | 0.50 | 0.11 | | 0.64 |
| Myristic acid | PI | 0.47 | 0.53 | 0.03 | 8 | 0.30 |
| vs Control | % | 0.48 | 0.61 | 0.08 | | 0.22 |

[a]skatole and myristic acid.
*Largest standard error of the means.
Control - feeder sprayed with mineral oil.
Molecule - feeder sprayed with skatole, myristic acid or both.

Weaning Trial.

Figure 4:
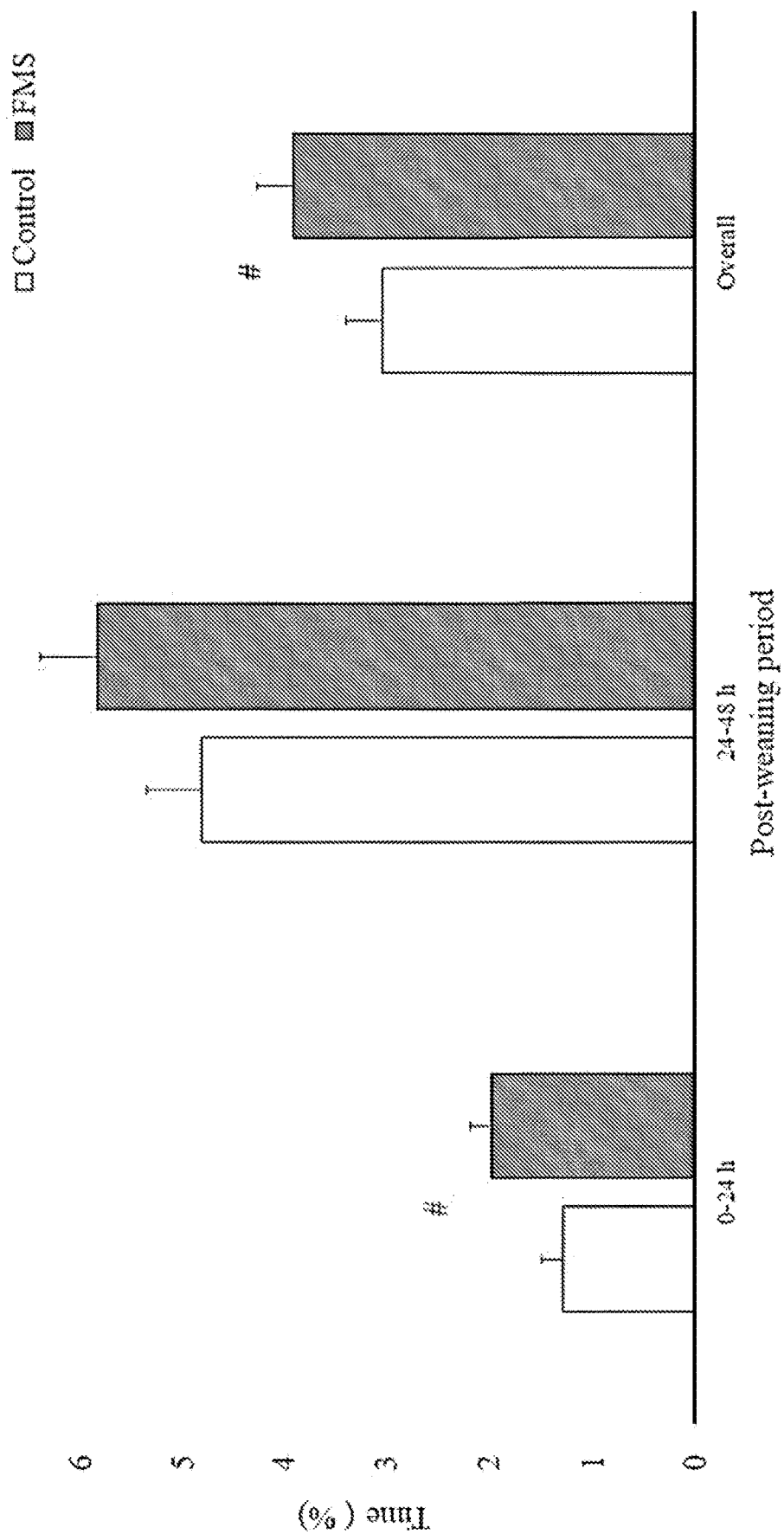
FIG. 4 is a plot showing the percentage of time+standard error control (n=12) and faecal maternal semiochemicals (FMS; n=12) treated pigs spent feeding during the first 48 hours post-weaning. #=a tendency to be statistically different ($0.05<P<0.10$).
Figure 5:
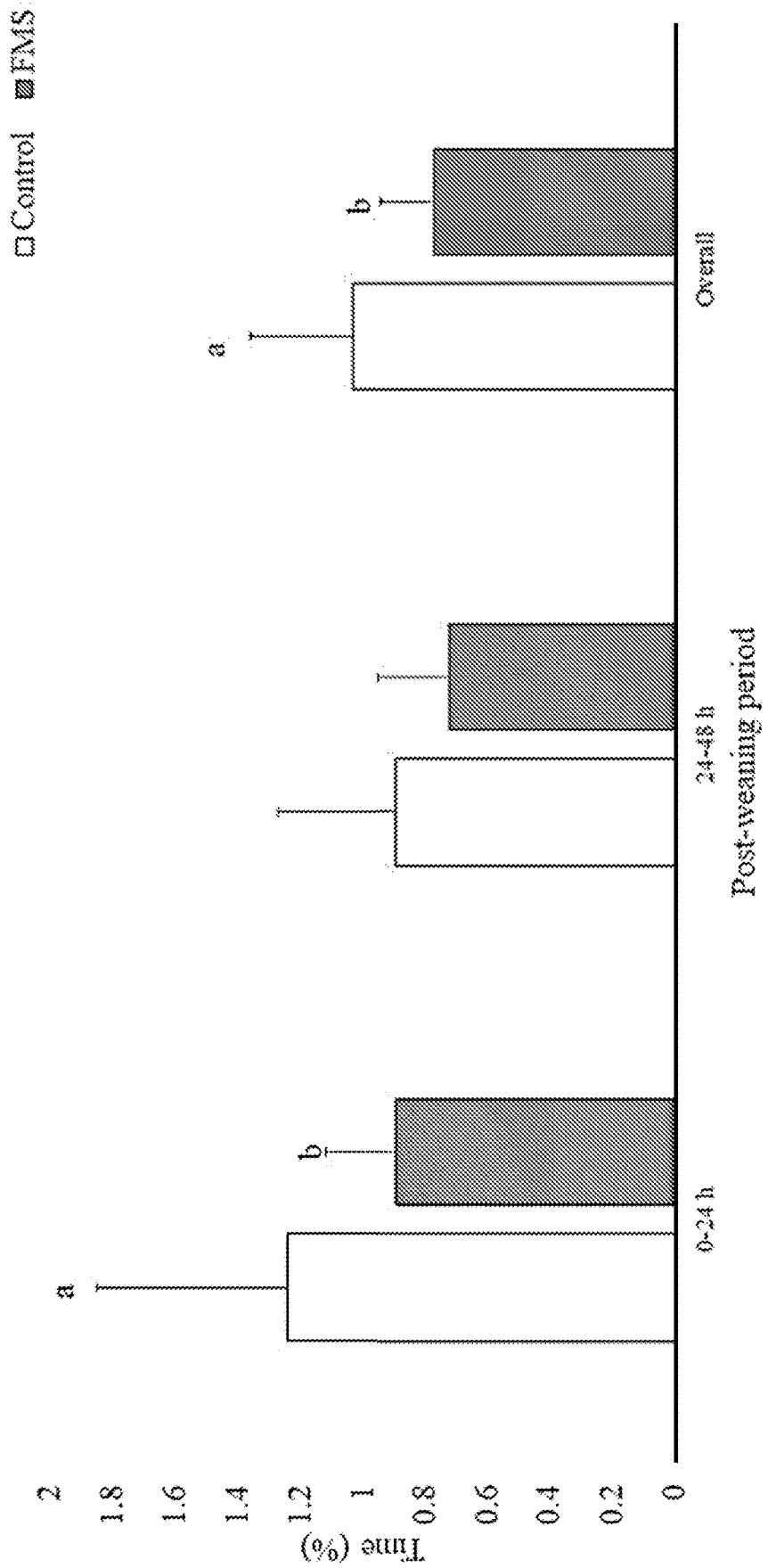
FIG. 5 is a plot showing the percentage of time+95% confidence interval control (n=12) and fecal maternal semiochemicals (FMS; n=12) treated engaged in aggressive behavior during the first 48 hours post-weaning. Bars with different superscript within period are significantly different from each other due to a treatment effect ($P<0.05$).

FIGS. 4 and 5 present a summary of piglets' feeding and aggressive behavior the first 48 hours post-weaning, respectively. Pigs exposed to the faecal maternal semiochemicals (FMS) spent significantly less time engaged in aggressive behavior during the first 24 hours post-weaning (P=0.03).

Faecal maternal semiochemicals tended to increase piglet feeding behavior the first 24 hours post-weaning (P=0.09). No differences in feeding or aggressive behavior were observed from 24 to 48 h post-weaning. Over the entire 48-hour period, FMS reduced pig aggression (P=0.04) and tended to increase feeding behavior (P=0.08). The interaction between treatment and time was not statistically significant for feeding and aggressive behavior. The time effect was significant only for feeding behavior where piglets spent more time eating in the 24-48 h period compared to the 0-24 h period (5.33±0.37% vs 1.64±0.14%; P=<0.01). There was no treatment effect on piglet body weight, average daily gain (0.35±0.02 kg vs 0.34±0.02 kg), and average daily feed intake (0.52±0.03 kg vs 0.55±0.03 kg) during the first 28 days post-weaning. There was a significant treatment effect on piglets Gain: Feed ratio. Control pigs had better Gain: Feed ratio (0.67±0.02 vs 0.62±0.02; P=0.02) compared to FMS treated pigs. The treatment by time interaction was not statistically significant for all performance variables measured.

Discussion

Changes in sow faecal volatile profile and nutrient content were evaluated during gestation and lactation to identify candidate maternal faecal semiochemicals and determine the nutritional value of lactating sow faeces. Sows reduced their feed intake during the first week of lactation. This was expected since a reduction in feed intake is usually observed after farrowing. During lactation, sow faeces had higher dry matter content. This could be a result of the reduction in feed intake since low feed intake reduces passage rate and increases faecal dry matter content. The increase in water requirements sows have during lactating promotes intestinal water absorption and could also increase faecal dry matter. During lactation the faecal concentration of certain nutrients and minerals changed. The reduction in $Ca^{2+}$ and $K^+$ faecal concentrations during lactation might be the result of the high levels of $Ca^{2+}$ and $K^+$ excreted in the milk. Lactating sow faeces contained higher concentration of true protein (TP). In this study, TP was defined as the amount of biological protein present in sow faeces that reacted to the Bicinchoninic acid assay (BCA), not the nitrogen percentage in the faeces. This is a more reliable measure since it does not quantify non-protein nitrogen in faeces. The increase of TP during lactation can be a result of the reduction in crude protein ileal digestibility that has been observed during lactation and the low feed intake sows had during the first days in lactation. In addition, the increased cortisol level associated with the farrowing process could promote gut protein synthesis thus leading to higher faecal protein content. The observed increase in faecal dry matter and the low faecal output during lactation could explain why some minerals and nutrients were in higher concentrations during lactation since undigested nutrients were clustered in a smaller volume. Further studies are required to evaluate the effect of sow physiological status on nutrients and minerals digestibility. Based on these results, consumption of maternal faeces will result in the ingestion of minerals and nutrients that could be beneficial to piglets. This could explain why deprivation of maternal faeces reduced piglet performance.

A total of 26 VOCs were found in sow faecal matter by GC/MS analysis. Pentanoic acid, 3-methylbutanoic acid, 4-methylphenol, 3-methylindole, and indole have been found in growing pig faeces and in piggeries' air, manure, slurry, and dust. Fourteen different fatty acid methyl ether (FAME) were found in sow faeces. Most of the FAMEs found in sow faeces are part of the whole-cell composition of swine faecal coliforms. Thus, it could be possible that FAMEs present in sow faecal extract came from bacterial membrane degradation during the extraction process. Further studies are needed to determine the origin of these FAMEs. Likewise, long chain saturated fatty acids such as tetradecanoic (myristic), pentadecanoic and hexadecenoic acids were found in sow faeces. Long chain fatty acids are commonly present in faeces since they are feed constituents. The faecal presence of these fatty acids has been used as an indicator of hind-gut bacterial activity.

Olfaction plays a critical role in piglet maternal recognition. It has been speculated that lactating sows emit faecal semiochemicals that attract piglets. The present study did not find a unique faecal semiochemical secreted by sows during lactation that might be acting as a chemical signal and thus attracting piglets and inducing coprophagy. Notwithstanding, the peak area ratio of seven molecules changed with sow physiological status. The peak area ratio and the estimated concentration of skatole and myristic acid significantly increased during lactation whereas the peak area ratio and the concentration of methyl octadeca-9,12-dienoate decreased during lactation. After correcting for faecal dry matter differences between periods, only the concentration of skatole and methyl linoleate significantly changed during lactation. Thus, the changes in dry matter content might explain the increase in concentration of myristic acid. In addition to these analytes, the peak area ratio of two unknown analytes significantly increased during lactation. These unknown analytes were not successfully identified in this study since candidate molecules analytical standards mass spectrum and retention time did not matched with the ones obtained in the samples.

Herein was found that skatole faecal concentration increased by almost three-fold during lactation. Skatole is commonly found in swine manure and, together with androstenone it causes the boar taint. Of all intestinal microbes, only *Clostridium* spp. and *Lactobacillus* spp. can degrade tryptophan or indole acetic acid into skatole.

In sows, skatole faecal concentration changes with the oestrus cycle. During oestrus, sows skatole faecal concentration increased from 12 to 50 μg/g DM. In this study, skatole concentration was correlated with sow feed intake and oestradiol and progesterone levels during oestrus. Moreover, in sows, high levels of growth hormone, insulin-like growth factor one (IGF-1), and glucocorticoids increased skatole faecal excretion because these hormones promote intestinal mucosal cell proliferation thus providing more substrate to the intestinal microflora.

In this study, skatole faecal concentration was estimated to increase from 11.69±1.86 μg/g during gestation to 31.29±1.86 μg/g during lactation. When expressed on dry matter basis, the estimated skatole faecal concentration in this study was higher than the one reported by Claus et al. This difference can be due to the physiological state of the animals used in both studies (pregnant and lactating vs non-pregnant sows) and the extraction procedure. Notwithstanding, in both studies, the increase in skatole concentration was close to three- and four-fold of magnitude during lactation and oestrus, respectively. The same hormonal and nutritional changes that increased skatole faecal concentration during oestrus might explain the increment in skatole faecal concentration after farrowing. For instance, after farrowing and in oestrus, sow progesterone levels decrease and sows tend to reduce their feed intake. In addition, early after farrowing, plasma cortisol, prolactin, growth hormone, and oxytocin increase. All these physiological changes might increase mucosal turnover promoting skatole synthesis by microbes. The observed increase of true protein in sow faeces after farrowing support this theory. Hormonal changes after farrowing could increase mucosal turnover providing more substrate to the bacteria thus increasing skatole faecal concentration.

Myristic acid concentration also increased during lactation. This could be due to the increase in faecal dry matter content observed after farrowing since no difference was found when the concentration was expressed on dry matter basis. To the author's knowledge, this change has not been reported previously in the literature. Surprisingly, myristic acid has been found in the secretion of sebaceous glands of sows, mares, bitches, cows, ewes, queens, and does. In mammals, a combination of fatty acids, including myristic acid, act as a maternal pheromone guiding newborn of the species mentioned above to the mammary gland. In pigs, myristic acid is also present in maternal fluids such as amniotic fluid, colostrum, and milk. The fact that reproductive hormones regulate skatole faecal concentration and that myristic acid is one of the constituents of domestic animal maternal pheromones supports the idea that these two molecules might be acting as maternal semiochemicals in lactating sow faeces. Since piglets have a very acute sense of smell, it is possible that by detecting changes in the concentration of these semiochemicals, they can discriminate between lactating and gestating sow faeces.

The behavioral tests conducted using skatole and myristic acid showed that piglets were attracted to a feeder sprayed with skatole and myristic acid compared to a control feeder. However, piglets were not attracted to the individual analytes. Since the major volatile difference between lactating and non-lactating sow feces was the increased in concentration of skatole and myristic acid, it is hypothesized that the increased in concentration of these analytes, might be acting as a multicomponent chemical signal in lactating sow feces.

Skatole has an attractant effect in different species. For instance, the mosquito *Culex quinquefasciatus* uses skatole as an organic signal to select oviposition site. In addition, skatole is one of the components of a synthetic pheromone fishers use to attract fish. In a similar way, myristic acid induces landing behavior in Culex nigrigalpus mosquitoes. With all of these, it makes sense to suggest that skatole and myristic acid could be acting as a multicomponent maternal signal attracting piglet to maternal faeces and potentially inducing coprophagy.

Believing that skatole and myristic acid could be acting as faecal maternal semiochemicals (FMS), the effects of spraying skatole and myristic acid on the weaning environment were assessed. Spraying weaned pig feeders with FMS reduced the percentage of time piglets engaged in aggressive behavior the first 24 h post-weaning by 28% and by 24% over the entire 48 h post-weaning period. No difference in aggressive behavior was observed from the 24-48 h period.

The application of FMS on pig feeders tended to increase feeding behavior the first 24 h post-weaning but did not change the apparent feed intake. A possible explanation of why feeding and aggressive behavior were not improved the second day post-weaning could be that after 24 h the FMS application frequency was reduced (i.e. every 12 h instead of every four hours). By decreasing the application frequency, it was possible that piglets were not continuously exposed to the semiochemicals and thus its attractant and calming effect was reduced. Another possible explanation to the lack of behavioral differences in the second day could be that piglets habituated to the semiochemicals. By being habituated to the stimuli, its innate response to maternal semiochemicals could be reduced.

The neural or physiological mechanism by which FMS exhibit a calming and attractant effect in piglets is still unknown. Little or no information is available about how pigs perceive skatole. Since skatole is a very volatile compound, it is most likely to be perceived by the main olfactory system. Myristic acid, on the other hand, could be perceived by both the main olfactory system and the accessory olfactory system. Four olfactory binding proteins that were involved in the perception of the pig appeasing pheromone were previously identified. Of these four olfactory binding proteins, the Von Ebner's gland protein, a protein present in the main olfactory system and vomeronasal organ mucosa, showed a strong affinity for fatty acids. Thus, it is possible that myristic acid could be perceived by both olfactory systems. A possible mechanism by which the FMS exhibit a calming effect could be that, when perceived by the vomeronasal organ, a calming stimulus is sent to the amygdala and this stimulus then could inhibit or reduce aggression.

Conclusion

Sow faecal nutrient content changed during lactation. Lactating sow faeces had higher true protein content and are rich in other nutrients and minerals that could be beneficial to piglets. Thus, coprophagy could result in the ingestion of nutrients and minerals that might have a positive impact on piglet performance and health. Twenty-six volatile organic compounds were identified in lactating and gestating sow faeces. No specific analyte was identified on each period. After farrowing, skatole and myristic acid faecal concentrations in fresh faeces increased by 2.68 and 1.13 folds respectively. Preference assessments showed that piglets had a preference for a feeder sprayed with a solution containing skatole and myristic acid. No preference was found when skatole and myristic acid were sprayed individually on the feeder. Spraying weaned pig feeders with skatole and myristic acid reduced the incidence of aggressive behavior and tended to increase feeding behavior the first 24 h post-weaning by 28% and 35% respectively.

Methods

Identification of Maternal Semiochemicals.

Texas Tech University Institutional Animal Care and Use Committee approved all animal handling, feeding, housing, and sampling procedures used in this study (protocol #16105-11). All procedures used in this study were in accordance with corresponding guidelines and regulation for the use of swine in research. Faecal samples were collected from PIC Camborough line sows (N=8) at the Texas Tech University Swine Research Facility. During gestation, all sows were housed in crates (2 m´0.6 m) and, ten days before the expected farrowing day, sows were moved to conventional farrowing crates (1.52 m´2.13 m). Sows were fed 6.8 kg of lactation diet from two weeks before the expected farrowing day until weaning. This was to prevent that differences in faecal volatile profile and nutritional analysis were not due to a change in diet or an increased feed intake during lactation.

Faecal samples were collected from the same animal during gestation and lactation. Faecal samples were collected daily for five consecutive days after a five days adaptation period to the lactation diet. Gestation faecal samples were collected starting at 10±2 days before the expected farrowing day. Lactation faecal samples were collected for five consecutive days after sow farrowed. Since the first two days after farrowing sows did not have faecal matter for collection, lactation samples were collected from day 3-7 after farrowing. All faecal samples were collected in the morning (0600) directly from the sows' rectum. Immediately after collection, samples were placed in a whirl-pack bag (Sigma-Aldrich, U.S.A), preserved in liquid nitrogen and transported to the lab. Once in the lab, frozen samples were pulverized, and aliquots of 2 g were prepared for liquid extraction and nutritional analysis. Samples and aliquots were stored at −80° C. until analysis. Liquid extraction was performed within two weeks after collection to prevent significant volatile loss[56].

Nutritional analyses of gestation and lactation faecal samples were conducted as a composite of the five samples collected in each period. Composites were dried for 48 h at 55° C., ground and sent by mail to Dairy One, Inc., (Ithaca, NY) for nutritional analyses. The concentration of true protein (TP) in faeces was measured using the bicinchoninic acid (BCA) assay kit (Thermo Fisher Scientific, Bellefonte, PA) following manufacture indications and Paul et al. protein extraction procedure. TP was defined as the amount of biological protein present in sow faeces that reacted to the BCA assay. This differed from the crude protein (CP) in that it does not take in consideration non-protein nitrogen.

The two gram aliquots were placed in a 15 mL falcon tube and mixed with 4 mL of methanol (100%) and 1 mL of a 500 µg/ml heptanoic acid solution as internal standard. Subsequently, samples were vortexed at high speed for two minutes and centrifuged at 3,000 rpm for 10 minutes at 15° C. Once centrifuged, 3 mL of the supernatant was filtered with a polytetrafluoroethylene (PTFE) 0.2 µm syringe filter and diluted in 100 mL of distilled water. After dilution, samples were pre-separated on a previously conditioned reversed phase HyperSep C18 SPE cartridge (2 g bed weight; 40-60 µm particle size; 60 Å pore size; 15 mL column capacity; Thermo Fisher Scientific, Bellefonte, PA). Cartridges were conditioned with 10 mL of 100% methanol followed by 10 ml of distilled water. After conditioning, the diluted sample (103 mL) was gradually loaded and filtered at a steady rate (~0.25 mL/sec) using a 12-valve vacuum manifold. After filtration, cartridges were washed with 10 mL of methanol: water solution (1:10 v/v). Filtered and washed material was discarded and analytes were eluted from the cartridge using 3 mL of tertbutyl methyl ether. Eluted material was centrifuged at 3,000 rpm for five minutes to separate the organic solvent from the aqueous layer. Subsequently, 300 µL of the organic solvent was transferred to a screw capped GC-vial.

A GC-MS (Thermo Trace GC-MS Ultra CA; Split/Splitless injection with ISQ Quadrupole Mass Spectrometry detector, Thermo Fisher Scientific Inc., San Jose, CA) was used to analyse faecal sample extracts. The instrument was equipped with an SPB-PUFA capillary column (30 m length 0.25 mm i.d.; film thickness 0.20 mm; Sigma-Aldrich, U.S.A) with bonded polyalkylene glycol stationary phase. Ultra-high purity helium was used as the carrier gas after it passed through a purification tramp at a flow rate of 1.2 mL/min with vacuum compensation. One micro-liter of the sample was injected by an auto sampler in the injection port in split-less mode. At the time of injection, inlet temperature was 250° C. Initial oven temperature was set at 140° C. and held constant for 2.5 minutes. Oven temperature was increased at a rate of 4° C./min until 210° C. and held constant for 35 minutes. The mass spectrometer ion source temperature was 225° C. during analysis and was operating on electron impact mode (70 eV) with scanning range of 45-450 amu. Compounds of interest were identified by comparing the obtained mass spectra from a total ion chromatogram with the instrument control software reference library. The identity of major peaks was further confirmed by comparing the mass spectra and retention time of analytical standards run under the same condition as the samples. Candidate semiochemicals concentrations were estimated using a 6-point calibration curve of the analytical standard at known concentrations. A regression line was calculated for each semiochemical and used to estimate its concentration in the samples.

The five gestation and lactation faecal samples were analysed by GC/MS individually. The instrument software (Xcalibur™, Thermo Fisher Scientific) calculated the area under each peak in the chromatogram. Each peak area was divided by the peak area of the internal standard (heptanoic acid) to obtain an area ratio. Data were analysed using SAS statistical software. For all variables, a normal distribution was confirmed using PROC Univariate. An exploratory analysis was conducted including sow as a block and collection day as a fixed effect. Since no statistically significant difference was found on the peak area ratio within periods (i.e. lactation or gestation), an average ratio was obtained for both periods (gestation and lactation) by averaging the area ratio of the five samples in each period. A paired sample t-test was used to evaluate significant differences in peak area ratio, analyte estimated concentration, and nutritional data between periods.

Preference Test.

Piglets used in this study were from a terminal cross between PIC Camborough genetic line sows and a terminal sire. Litters were housed in conventional slatted floor farrowing crates (1.52 m×2.13 m). All piglets were ear notched, teeth clipped, and injected with iron at 3 days of age. During this day, all males within a litter were also castrated by farm personnel. Prior to the study, piglets had no creep feeder. The preference test was performed in their home farrowing crate. Preference tests were conducted to determine piglet preference for skatole and myristic acid. First, nine litters (105 piglets) were used to evaluate piglet preference toward a solution containing both, skatole and myristic acid (N=9). Once piglet preference for a solution containing both molecules was determined, 8 litters (79 piglets) were used to evaluate piglet preference for skatole (N=8) and another 8 litters (80 piglets) to evaluate piglet preference for myristic acid (N=8) individually. Each litter was tested only once to ensure that piglets were tested at the same age and that they were not previously exposed to a feeder or a semiochemical.

Figure 6:
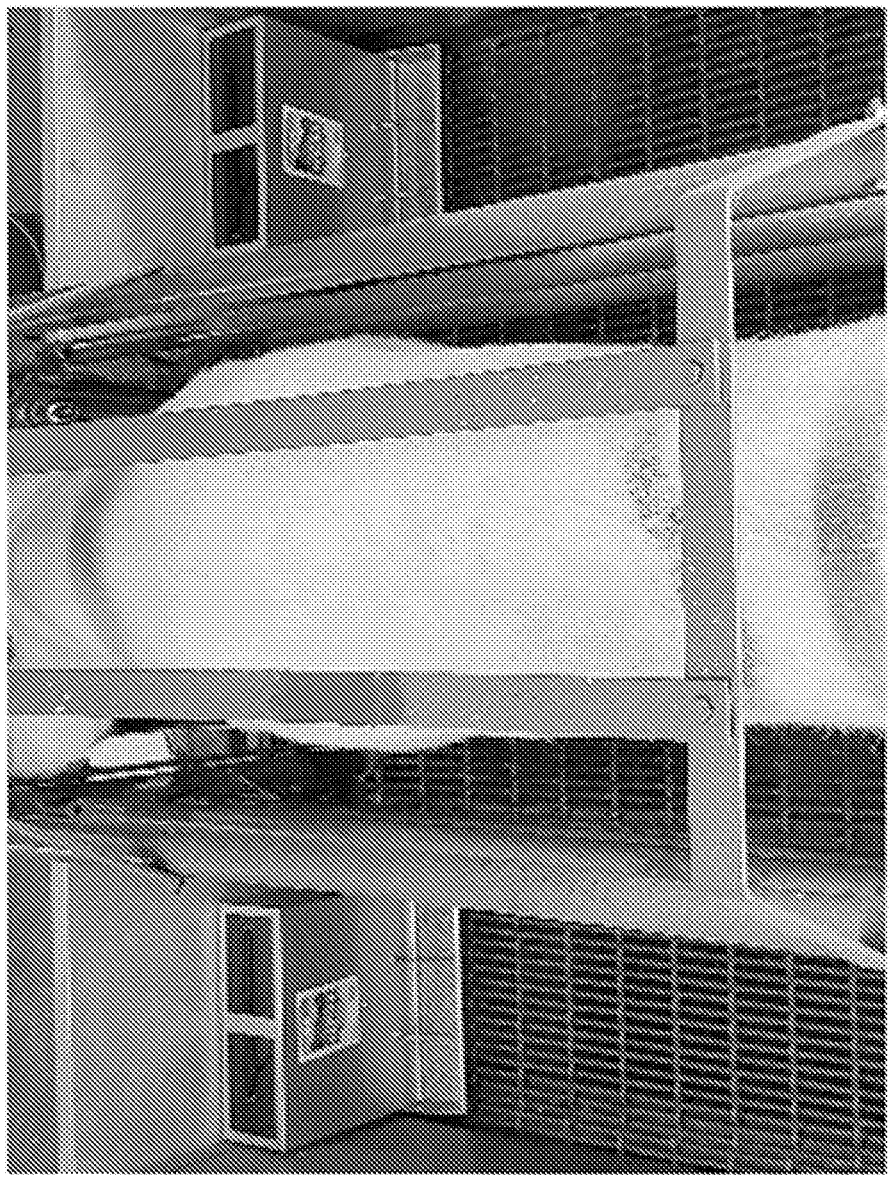
FIG. 6 is a photograph showing preference test setting. The two feeders were placed in front of the crate and the sow was facing the feeders. Sow was with the litter during the five-hour testing period.

At 7±2 days of age, two three-hole galvanized steel baby pig feeders were placed at each front corner of the farrowing crate for five hours for two consecutive days (FIG. 6). All trials were performed in the morning when piglets were more active. The sow was present during each five hours trial. Each feeder contained 100 g of pig pre-starter (Moorman's ShowTec Prestarter, ADM, Quincy, IL) and was sprayed with either 5 mL of mineral oil (control) or 5 mL of the testing solution. The solution was sprayed on the feeder and not the feed. The 5 mL of the testing solution contained 4.5 mg of skatole and/or 9.0 mg of myristic acid. This concentration was selected based on the estimated concentration of each analyte in 150 g of lactating sow faeces based on GC/MS analysis. On the second testing day, feeder locations were switched to correct for side biases. A single observer following a 30 second scan sampling method, observed the behavior of each piglet in the litter at 30 second intervals to determine the percentage of time piglets spent interacting with each feeder during the five-hour period each testing day. A total of 600 observations were recorded per litter in each testing day. The percentage of time piglets within a litter spent interacting with each feeder was calculated by dividing the number of time piglets were observed interacting with a feeder over the total number of observations. Interacting with the feeder was defined as when piglets were sniffing, touching or licking the area of the feeder sprayed with the solution or eating or rooting the feed. A preference index was calculated for each feeder by dividing the amount of time piglets were observed interacting with a feeder by the sum of the number of times piglets were observed interacting with both feeders.

For each litter (experimental unit), an overall feed intake, preference index, and percentage of time interacted with each feeder was obtained from both testing days. Difference in overall feed intake, preference index, and percentage of time piglets spent interacting with the control and the feeder sprayed with the testing solutions were analyzed using the Wilcoxon-singed ranked test. A preference was determined if piglets ate and/or interacted significantly more time with the feeder sprayed with the testing solution. An aversion towards the testing solutions was determined if piglets ate and/or interacted significantly less time with the feeder sprayed with the testing solution. All statistical analyses were performed using SAS 9.4. (SAS Inst., Inc., Cary, NC). A statistically significant difference was based on a P value≤0.05.

Weaning Trial.

Ninety-six piglets (48 borrows and 48 gilts) from a terminal cross between PIC Camborough genetic line sows and a terminal sire were randomly selected from 14 litters. At 25±2 d of age, piglets were weighed, blocked by weight [heavy 8.4±0.14 kg (32 pigs), medium 7.31±0.08 kg (32 pigs), and light 6.26±0.11 kg (32 pigs)], weaned, and randomly assigned (within block) to be treated with either mineral oil (control) or a solution containing skatole and myristic acid as maternal semiochemicals (FMS). Pigs where blocked by weight to reduce size variation within a pen. Pigs were housed in groups of four (i.e. 2 barrows and 2 females) non-littermate pigs per pen (24 pens total). Raised pens measuring 1.5×1.5 m with slat plastic floors were used in this study. Control and FMS treated animals were housed in separate rooms to prevent cross-contamination with the odor between treatments. Piglets had ad libitum access to feed and water and were fed a corn-soybean based diet that met nursing piglet nutrient requirements (NRC, 2012). Control pigs were exposed to mineral oil whereas the FMS treated pigs were exposed to 4.5 mg of skatole and 9.0 mg of myristic acid diluted in five ml of mineral oil as in the preference test. Five ml of the FMS or mineral oil were sprayed on the feeder of each pen after the weaning was concluded. Treatments were reapplied on the feeders every four hours until 12 h post-weaning. After 12 h post-weaning, feeders were sprayed every 12 h until 48 h.

All pens (i.e. 12 control and 12 FMS) were video recorded for the first 48 h post-weaning. A single observer evaluated both group feeding and aggressive behavior from 0-24 hours and from 24-48 hours post-weaning using a scan sample technique at one-minute intervals. A total of 2880 observations were recorded from each pen during the 48-hour period. The percentage of time piglets within a pen spent feeding or displaying aggressive behavior was calculated by dividing the number of times piglets within a pen were observed doing one of these behavior over the total number of observations. Aggressive behavior were defined as when two or more piglets were biting or pushing each other. Feeding behavior was defined as when piglet's head was inside the feeder trough.

Piglet average daily feed intake, average daily weight gain, and Gain:Feed ratio were measured weekly for four weeks to determine any treatment effect on piglet performance. Average daily feed intake was calculated by estimating weekly feed consumption by weighing the remaining feed on the feeder. Average daily gain was calculated by weekly changes in piglet body weight. Gain:Feed ratio was the ratio between average daily gain and average daily feed intake.

For all statistical analyses the pen was considered the experimental unit (n=12). Statistical analyses were conducted using SAS 9.4 statistical software. All behavior and performance data were tested for normality and homoscedasticity. Due to the lack of normality in aggressive behavior data, its' statistical analysis was conducted on the inversed transformed data. The back transformed data was reported. Performance and behavioral data were analysed as a complete randomized block design using repeated measures analysis of variance (ANOVA). The model included the effect of time, treatment, and their interaction as fixed effects and pen and weight block as a random effect. There was no treatment by block interaction. Tukey Kramer post hoc test was used for multiple comparisons. A statistically significant difference was based on a P value≤0.05.

The invention claimed is:

1. A formulation administered to a suid for reducing aggression and improving feeding behavior in the suid, the formulation comprising a pheromonal agent consisting of the combination of 3-methylindole (skatole) and myristic acid, wherein the amount of 3-methylindole (skatole) administered to the suid is between about 0.01 to about 5 mg/ml (w/v) of the formulation and the amount of myristic acid administered to the suid is between about 0.02 to about 10 mg/ml (w/v) of the formulation.

2. The formulation of claim 1, wherein the suid is a lactating piglet.

3. The formulation of claim 1, wherein the suid is a weaned piglet.

4. The formulation of claim 1, wherein the formulation is formulated in a feed composition for oral administration to a suid.

5. The formulation of claim 4, wherein the feed composition is in the form of an aerosol spray, a pump spray, or a diffuser.

6. The formulation of claim 1, wherein the formulation further comprises at least one additional component selected from the group consisting of a solvents, a propellant, a surface-active agent, an emulsifier, a foaming agent, a preservative, a fragrance, and combinations thereof.

7. The formulation of claim 1, wherein the formulation further comprises at least one additional component selected from the group consisting of a nutritive agent, a pharmaceutical agent, and combinations thereof.

8. The formulation of claim 7, wherein the pharmaceutical agent is selected from the group consisting of a vitamin, a mineral, an amino acid, an antioxidant, a probiotic, an essential fatty acid, and a pharmaceutically acceptable excipient.

9. The formulation of claim 8, wherein the pharmaceutically acceptable excipient is selected from the group consisting of a non-effervescent disintegrant, a coloring agent, a flavor-modifying agent, an oral dispersing agent, a stabilizer, a preservative, a diluent, a compaction agent, a lubricant, a filler, a binder, taste-masking agents, an effervescent disintegration agent, and combinations thereof.

10. The formulation of claim 9, wherein the lubricant is selected from the group consisting of magnesium stearate, calcium stearate, zinc stearate, hydrogenated vegetable oils, sterotex, polyoxyethylene monostearate, talc, polyethyleneglycol, sodium benzoate, sodium lauryl sulfate, magnesium lauryl sulfate, and light mineral oil.

* * * * *